US012716623B2

(12) United States Patent
Zhou et al.

(10) Patent No.: US 12,716,623 B2
(45) Date of Patent: Aug. 25, 2026

(54) THERMOELECTRIC COOLING ASSEMBLY AND BEAUTY INSTRUMENT

(71) Applicant: SHENZHEN JVK MEDICAL INSTRUMENTS CO., LTD., Shenzhen City (CN)

(72) Inventors: Ying Zhou, Shenzhen City (CN); Bing Li, Shenzhen City (CN)

(73) Assignee: SHENZHEN JVK MEDICAL INSTRUMENTS CO., LTD., Shenzhen City (CN)

( * ) Notice: Subject to any disclaimer, the term of this patent is extended or adjusted under 35 U.S.C. 154(b) by 352 days.

(21) Appl. No.: 18/488,980

(22) Filed: Oct. 17, 2023

(65) Prior Publication Data

US 2024/0125523 A1 Apr. 18, 2024

(30) Foreign Application Priority Data

Oct. 17, 2022 (CN) ......................... 202211269145.2
Nov. 21, 2022 (CN) ......................... 202211473227.9
Nov. 21, 2022 (CN) ......................... 202223107610.0

(51) Int. Cl.
*F25B 21/02* (2006.01)
*A45D 26/00* (2006.01)
*A61N 5/06* (2006.01)

(52) U.S. Cl.
CPC .............. *F25B 21/02* (2013.01); *A45D 26/00* (2013.01); *A61N 5/0616* (2013.01);
(Continued)

(58) Field of Classification Search
CPC .. F25B 21/02; F25B 2321/0252; A45D 26/00; A45D 2026/008; A45D 2200/15;
(Continued)

(56) References Cited

U.S. PATENT DOCUMENTS

2006/0289662 A1* 12/2006 Dessiatoun ........... H01L 23/473 257/E23.098
2009/0287195 A1* 11/2009 Altshuler ........... A46B 15/0036 606/9
2021/0393014 A1* 12/2021 Pan ........................ H10N 10/13

FOREIGN PATENT DOCUMENTS

CN 201732326 U 2/2011
CN 212308030 U 1/2021
(Continued)

*Primary Examiner* — Niketa Patel
*Assistant Examiner* — Sebastian X Lukjan
(74) *Attorney, Agent, or Firm* — Cheng-Ju Chiang

(57) ABSTRACT

The present invention provides a beauty instrument, comprising: a housing with vents therethrough as an air inlet or air outlet; a control circuit board in the housing; a light source assembly in the housing and electrically connected with the control circuit board; and a thermoelectric cooling assembly. The thermoelectric cooling assembly comprises: a thermoelectric cooler, a heat sink, a fan, and a heat transfer assembly. The heat transfer assembly comprises a VC or an ALVC or an Aluminum Heat Pipe. The heat transfer assembly is thermally connected between the heat sink and the hot side of thermoelectric cooler. A front end of the beauty instrument has a light outlet surface; the cold side is connected to and cool the light outlet surface, or the cold side serves as the light outlet surface, thereby, the light outlet surface is able to cool skin in contact.

19 Claims, 12 Drawing Sheets

(52) U.S. Cl.
CPC .... *A45D 2026/008* (2013.01); *A45D 2200/15* (2013.01); *F25B 2321/0252* (2013.01)

(58) Field of Classification Search
CPC ............ A61N 5/0616; A61N 2005/007; A61N 2005/0644; A61B 2018/00017; A61B 18/203; A61B 2018/00047; A61B 2018/0047; A61B 2018/00476; A61B 2018/1807
See application file for complete search history.

(56) References Cited

FOREIGN PATENT DOCUMENTS

| | | | | | |
|---|---|---|---|---|---|
| CN | 213430517 | U | | 6/2021 | |
| CN | 213697442 | U | | 7/2021 | |
| CN | 215821349 | U | | 2/2022 | |
| CN | 216163139 | U | | 4/2022 | |
| CN | 216258753 | U | | 4/2022 | |
| CN | 216282138 | U | | 4/2022 | |
| CN | 216566016 | U | | 5/2022 | |
| CN | 217138253 | U | | 8/2022 | |
| CN | 219243958 | U | | 6/2023 | |
| EP | 4029561 | A1 | | 7/2022 | |
| JP | 2014-28130 | A | | 2/2014 | |
| JP | 2019-520901 | A | | 7/2019 | |
| JP | 3239176 | U | | 9/2022 | |
| KR | 20-2021-0000127 | U | | 1/2021 | |
| KR | 20-0495286 | Y1 | | 4/2022 | |
| WO | 2018/003957 | A1 | | 1/2018 | |
| WO | WO-2021196506 | A1 | * | 10/2021 | ............... A61N 5/06 |

* cited by examiner (a) (b)

THERMOELECTRIC COOLING ASSEMBLY AND BEAUTY INSTRUMENT

CROSS REFERENCE TO RELATED APPLICATIONS

The present invention is a 35 U.S.C. § 119 benefit of earlier filing date; right of priority of Chinese Application No. 202211269145.2, filed on Oct. 17, 2022; Chinese Application No. 202211473227.9, filed on Nov. 21, 2022; and Chinese Application No. 202223107610.0, filed on Nov. 21, 2022; the disclosures of which are incorporated by reference herein.

BACKGROUND OF THE INVENTION

Field of the Invention

The present invention relates to the field of beauty devices, and particularly relates to a thermoelectric cooling assembly and a beauty instrument.

Description of Related Art

The existing beauty instrument that uses pulsed light or laser or other light sources to achieve beauty functions. The light emitted by the light source irradiates the skin surface in contact with the light outlet of the beauty instrument head for skin beauty, such as hair removal, skin rejuvenation, spot removal, anti-inflammation, blood vessel softening, wrinkle removal, skin redness removal, acne treatment, vascular lesions treatment, pigmented skin lesions treatment or other functions. Some portable or handheld beauty instruments currently on the market have poor heat dissipation, which affects the work of the beauty device and cannot achieve the expected beauty effect; the structure of the beauty device is complex, and the light outlet of the beauty device head is poorly cooled, which results in burning the skin and provides a poor user experience.

BRIEF SUMMARY OF THE INVENTION

An object of the present invention is to provide a thermoelectric cooling assembly and a beauty instrument thereof, which aims to solve the problem that the existing beauty device has complex structure, and has the light outlet of the beauty instrument head are poorly cooled.

In a first aspect, the present invention provides a thermoelectric cooling assembly comprising a thermoelectric cooler, a heat sink, and a heat transfer assembly. The thermoelectric cooler comprises semiconductors in the middle and electrically interconnected by thermoelectric legs, a hot side and a cold side at both sides of the semiconductors. The heat transfer assembly comprises a Vapor Chamber or an Aluminum Vapor Chamber or an Aluminum Heat Pipe. The heat transfer assembly is thermally connected with the heat sink for heat dissipation; and the heat transfer assembly is thermally connected with the hot side or provides the hot side to which the thermoelectric legs is welded.

In a second aspect, the present invention provides a beauty instrument, comprising: a housing with vents therethrough as an air inlet or air outlet; a control circuit board in the housing; a light source assembly in the housing and electrically connected with the control circuit board; and a thermoelectric cooling assembly. The thermoelectric cooling assembly comprises: a thermoelectric cooler, a heat sink, a fan, and a heat transfer assembly. The heat transfer assembly comprises a Vapor Chamber or an Aluminum Vapor Chamber or an Aluminum Heat Pipe. The heat transfer assembly is thermally connected with the heat sink for heat dissipation, is thermally connected with the hot side or forms the hot side to which the thermoelectric legs is welded, and is located at a vent of the fan or serves as a part of the casing of the fan; a front end of the beauty instrument has a light outlet surface; the cold side of the thermoelectric cooler is connected to and cool the light outlet surface, or the cold side serves as the light outlet surface, thereby, the light outlet surface is able to cool skin in contact.

The thermoelectric cooling assembly and the beauty instrument of the present invention have advantages that:

- the thermoelectric cooling assembly of the present invention has a hot side of the thermoelectric cooler is connected to the heat sink in a way of rapid heat transfer through a Vapor Chamber (short for VC), an Aluminum Vapor Chamber or an Aluminum Heat Pipe, so that the hot side can quickly dissipate heat, a higher the temperature difference between the hot side and the cold side of the thermoelectric cooler is obtained, and a lower temperature of the cold side is obtained;
- the beauty instrument of the present invention comprises the thermoelectric cooling assembly above to cool the light out surface of the beauty instrument head, and provides a better cooling effect to the skin in contact with the light out surface.

Further, the thermoelectric cooling assembly is also used for heat dissipation of the light source assembly, effectively improving the heat dissipation efficiency.

In some embodiments, the thermoelectric cooler of the beauty instrument has the hot side thereof arranged on an outer wall of the Vapor Chamber, or the outer wall of the Vapor Chamber is directly used as the hot side of the thermoelectric cooler; and the Vapor Chamber is assembled to a fan, which effectively improves the heat dissipation efficiency for the beauty instrument and improves the cooling efficiency of the light outlet surface, so as to improve the beauty effect and the use experience. Further, the beauty instrument has a simple structure.

DETAILED DESCRIPTION OF THE INVENTION

Figure 1:
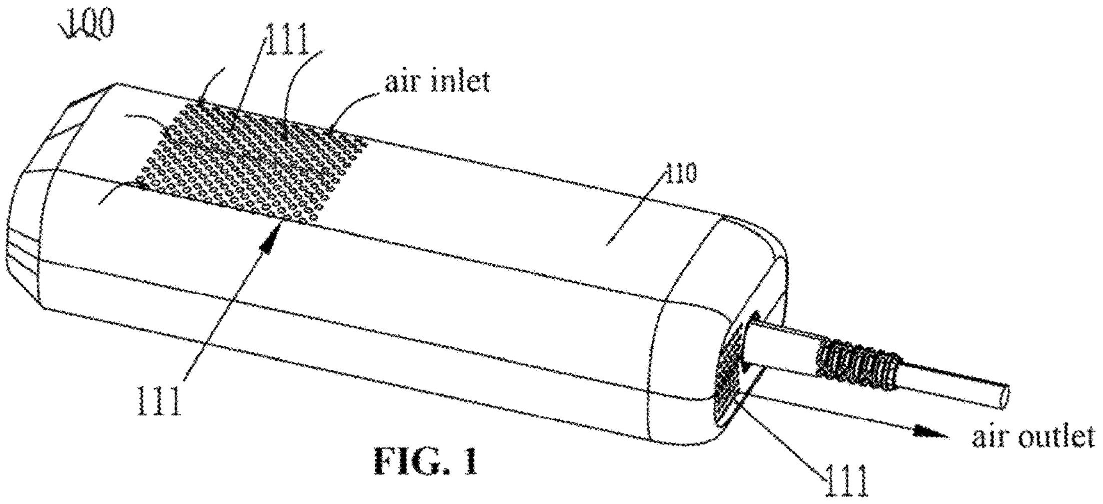
FIG. 1 is a perspective view of a beauty instrument in accordance with a first embodiment of the present invention.
Figure 2:
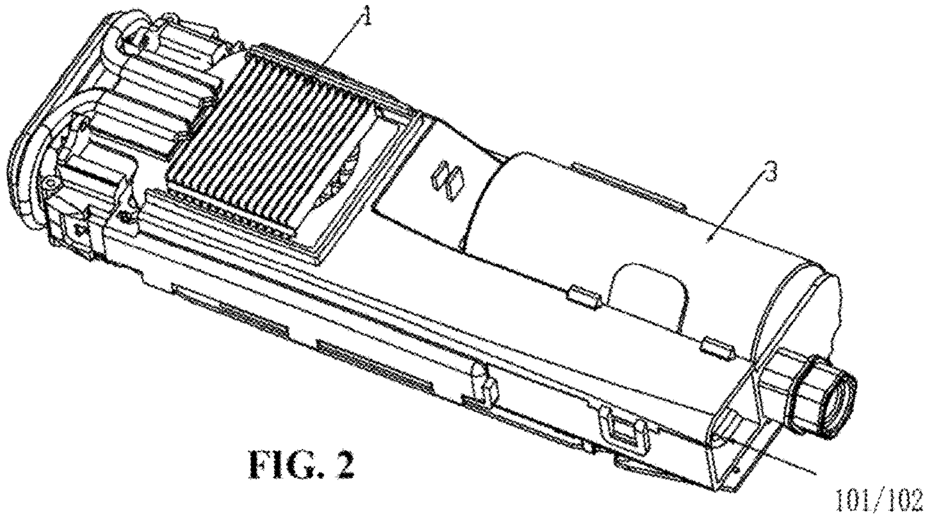
FIG. 2 is a perspective view of FIG. 1 with an upper shell removed.
Figure 3:
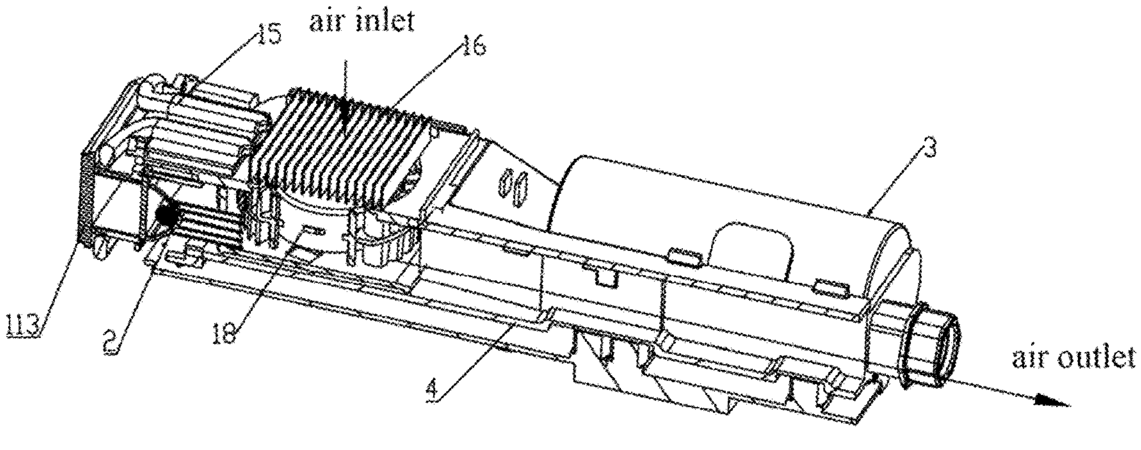
FIG. 3 illustrates an internal structure of the beauty instrument of FIG. 1.
Figure 4:
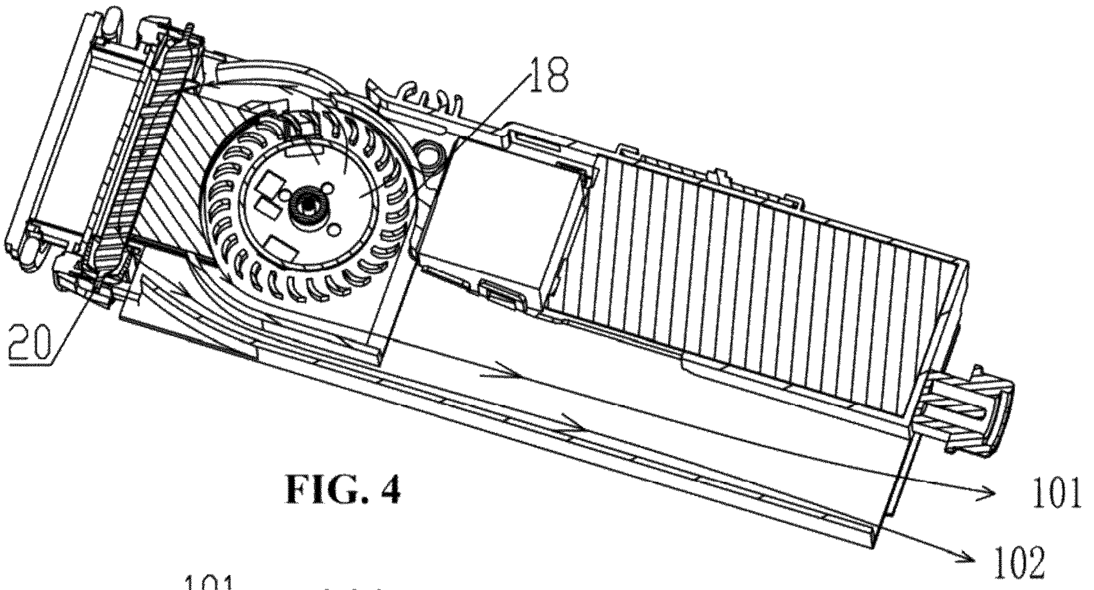
FIG. 4 illustrates an air flow path in the beauty instrument in accordance with the first embodiment of the present invention.

Referring to FIGS. 1-28, the present invention provides a thermoelectric cooling assembly 1 and a beauty instrument using the thermoelectric cooling assembly 1. The thermoelectric cooling assembly 1 comprises a thermoelectric cooler 10 for cooling a light out surface 113 of the beauty instrument head. The thermoelectric cooler 10 comprises semiconductors in the middle and a hot side 11' and a cold side 13 at both ends; the thermoelectric cooling assembly further comprises a heat transfer assembly 19 and a heat sink 16. The heat transfer assembly 19 comprises a Vapor Chamber 11 or an Aluminum Vapor Chamber or Aluminum Heat Pipe 191. The heat transfer assembly 19 is connected between the heat sink 16 and the hot side 11' of the thermoelectric cooler 10 for rapid heat transfer, so that the hot side can quickly dissipate heat.

Two ends of the Aluminum Vapor Chamber or Aluminum Vapor Chamber 191 are sealed, and refrigerant is sealed inside the Aluminum Vapor Chamber or Aluminum Vapor Chamber 191. Inner wall of the Aluminum Vapor Chamber or Aluminum Vapor Chamber 191 forms micro grooves 1911; and micropores 1912 are formed inside Aluminum wall of the Vapor Chamber or Aluminum Vapor Chamber.

Please refer to FIGS. 1-19, a beauty instrument 100 of the present invention comprises a housing, and a thermoelectric cooling assembly 1, a light source assembly 2, a battery 3 and a control circuit board 4 in the housing. The housing may define one or more vents 111 in the same or different positions of the housing in the form of honeycomb holes, a gap, a hole or others as air inlets and air outlets. The light source assembly 2 and the battery 3 are electrically connected to the control circuit board 4. The one or more vents 111 used for air inlet and outlet communicate with the space in the housing to form an air flow path (referring to the lines with arrows shown with arrows in FIGS. 4-6) for heat dissipation. A front end or a head of the beauty instrument 100 has a light out surface 113. The light out surface 113 can be in direct contact with the skin. Light emitted from the light source assembly 2 is transmitted through the light out surface 113 to irradiate skin for beauty treatment.

Referring to FIGS. 8-14, the thermoelectric cooling assembly 1 in accordance with the embodiment of the present invention is mainly used for cooling the light out surface 113 of the beauty instrument 1 to achieve a cold compress effect on the skin. The thermoelectric cooling assembly 1 comprises a thermoelectric cooler 10. The thermoelectric cooler 10 operates by the Peltier effect, and comprises semiconductors (alternating p & n-type semiconductor pillars) 12 in the middle and a hot side 11' and a cold side 13. The conductors comprise alternating p & n-type semiconductor pillars are placed thermally in parallel to each other and electrically in series and then joined with a thermally conducting plate on each side as the hot side and the cold side. The alternating p & n-type semiconductor pillars are interconnected by thermoelectric legs. The thermoelectric legs are thermally in parallel and electrically in series, and are welded to the hot end and cold end respectively. The thermoelectric cooler has positive and negative electrodes electrically connected to the control circuit board 4. In specific embodiments, the thermoelectric cooler 10 (specifically, the cold side 13) can be directly used as the light out surface 113, or used to cool the light out surface 113. When the thermoelectric cooler 10 is directly used as a light out surface, the cold side can be a transparent substrate such as a transparent crystal for light transmission as the light out surface 113, or the thermoelectric cooler 10 are annular for light transmission. When the thermoelectric cooler 10 is used to cool the light out surface 113, the cold side 13 of the thermoelectric cooler 10 contacts the light out surface 113, for example, is arranged around the light out surface. Alternatively, the cold side 13 of the thermoelectric cooler 10 is in contact with the light out surface 113 or connected with the light out surface through a heat transfer component. A heat transfer component 15 can quickly transfer the heat from the light out surface to the thermoelectric cooler 10 to achieve the cooling effect of the light out surface. The heat transfer component may be a thermal conductor such as (not limited to) made of metal material, such as a copper tube or a copper plate; or the heat transfer component may be a heat pipe or Vapor Chamber (VC) or others. The heat pipe or Vapor Chamber or other heat transfer components connecting the thermoelectric cooler 10 (cold side 13) and the light out surface 113 has a shape adapted for the thermoelectric cooler 10 or the cold side 13 for rapid heat dissipation. The light out surface 113 may be made of transparent material such as transparent crystal. The light out surface 113 may be annular with the annular central through hole transmitting light, and the material is not limited.

A heat pipe or Vapor Chamber operates in a principle of the evaporation and condensation of refrigerant medium in an enclosed vacuum tube or vacuum plate, and using fluid capillary action for heat dissipation and obtain a cooling function, which has such advantages as high heat transfer efficiency, excellent isothermal properties, heat flow density variability, and heat flow reversibility.

With reference to FIGS. 7-11, in a preferred embodiment, the cold side 13 of the thermoelectric cooler 10 is connected with the light out surface 113 through a heat transfer component 15 for rapid heat transfer. For example, the heat transfer component 15 is a heat pipe. For a better cooling effect, the heat transfer component (heat pipe) 15 forms an annular shape in close contact with the light out surface 13 and has both straightly extending ends in close contact with the cold side 13 so as to quickly transfer heat from the light out surface 113 to the thermoelectric cooler 10.

The heat generated by the hot side 11' of the thermoelectric cooler 10 may be discharged out of the beauty instrument 100 through air flow, and preferably using heat sink 16 to enhance heat dissipation. The heat sink 16 is provided on a Vapor Chamber 11. The hot side 11' of the thermoelectric cooler 10 is provided on an outer wall of the Vapor Chamber 11, or, the out wall of the Vapor Chamber 11 directly forms the hot side 11' of the thermoelectric cooler 10. The Vapor Chamber 11 is used for heat dissipation of the thermoelectric cooler 10. The Vapor Chamber 11 is located in the air flow path in the beauty instrument 100. When the thermoelectric cooler 10 is arranged on the Vapor Chamber 11, the hot side 11' of the thermoelectric cooler 10 is attached on the outer wall of the Vapor Chamber, so that the heat on the hot side is directly transferred to the Vapor Chamber 11; or, the hot side 11' of the thermoelectric cooler is set on the outer wall of the Vapor Chamber through a thermal conductor, and the heat from the hot side 11' is quickly conducted to the Vapor Chamber 11 through the thermal conductor. Alternatively, the thermoelectric legs of the thermoelectric cooler are welded to the outer wall of the Vapor Chamber 11 so that the outer wall is used as the hot side of the thermoelectric cooler 10. The Vapor Chamber 11 comprises a bottom plate, a frame and a cover plate to form a closed flat cavity which contains refrigeration medium therein and has capillary structures on an inner wall thereof. For a non-limiting example, one end of the Vapor Chamber 11 forms an extended platform for installing the thermoelectric cooler 10 or forming the hot side 11'. The area of the Vapor Chamber 11 is larger than the semiconductors 12 and the cold side 13 so as to increase the heat dissipation area.

The heat sinks 16 is provided on the Vapor Chamber 11. Preferably, the Vapor Chamber 11 is located in the housing of the beauty instrument 100 and behind the vents 111 thereof; the heat sink 16 on the Vapor Chamber 11 faces the vents 111. The heat sink 16 comprises one or more sets of heat conductive fins. The position, quantity and arrangement of the heat conductive fins can be set according to the internal space of the housing of the beauty instrument. With reference to FIGS. 10-15, the Vapor Chamber 11 is used as a top cover of the fan 18, the heat sink 16 comprises a set of parallel fins set on one side or both side of the Vapor Chamber 11; alternatively, the Vapor Chamber 11 is used as a side frame of the fan around the fan blade, the heat sink 16 comprises a set of fins set on the inner wall (the Vapor Chamber) of the fan 18 and curved along the direction of fan blade rotation (FIG. 15(*a*)); alternatively, the Vapor Chamber 11 is used as a top cover of the fan 18, which can be an annular flat plate and forms air inlet or outlet of the fan in center, the heat sink 16 comprises a set of fins arranged along an annular edge of the Vapor Chamber 11, and the fins can be arranged along radiation directions or at a certain angle to the radiation directions (FIG. 15(*b*)).

The thermoelectric cooling assembly 1 of the present invention further comprises a fan 18. The fan 18 is located in the air flow path in the beauty instrument and is used to enhance heat dissipation (cooling) efficiency. The fan 18 comprises a casing 180 and rotatable blades 181 installed in the internal cavity of the casing 18. The casing 180 can define vents 182 used for air inlet or air outlet in air communication with the internal cavity of the casing 180 to form an air flow path of the fan 18 which is in air communication with the air flow path in the housing of the beauty instrument 100. The Vapor Chamber 11 may be part of the casing 180 or installed on the casing 180.

Figure 12:
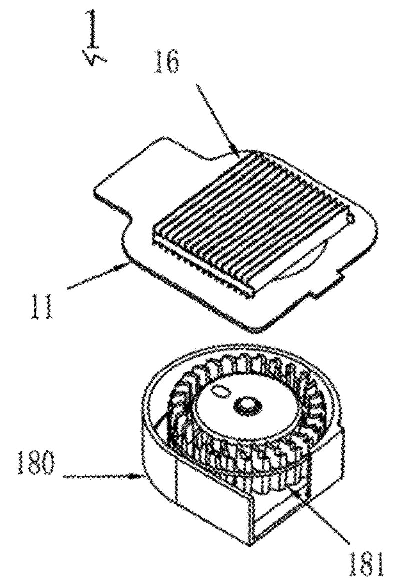
FIG. 12 is a partly exploded view of a fan in the thermoelectric cooling assembly of the present invention.
Figure 13:
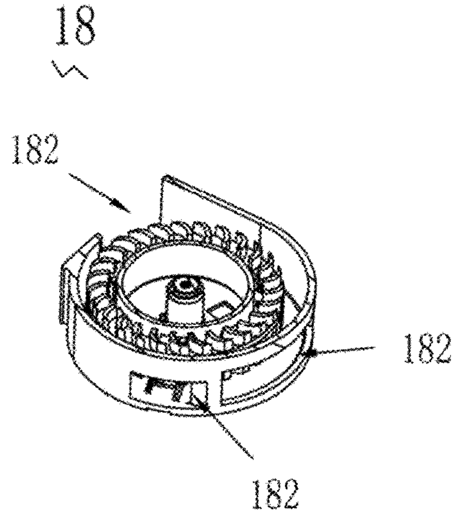
FIG. 13 is a perspective view of the fan without the Vapor Champer in the thermoelectric cooling assembly of the present invention.
Figure 14:
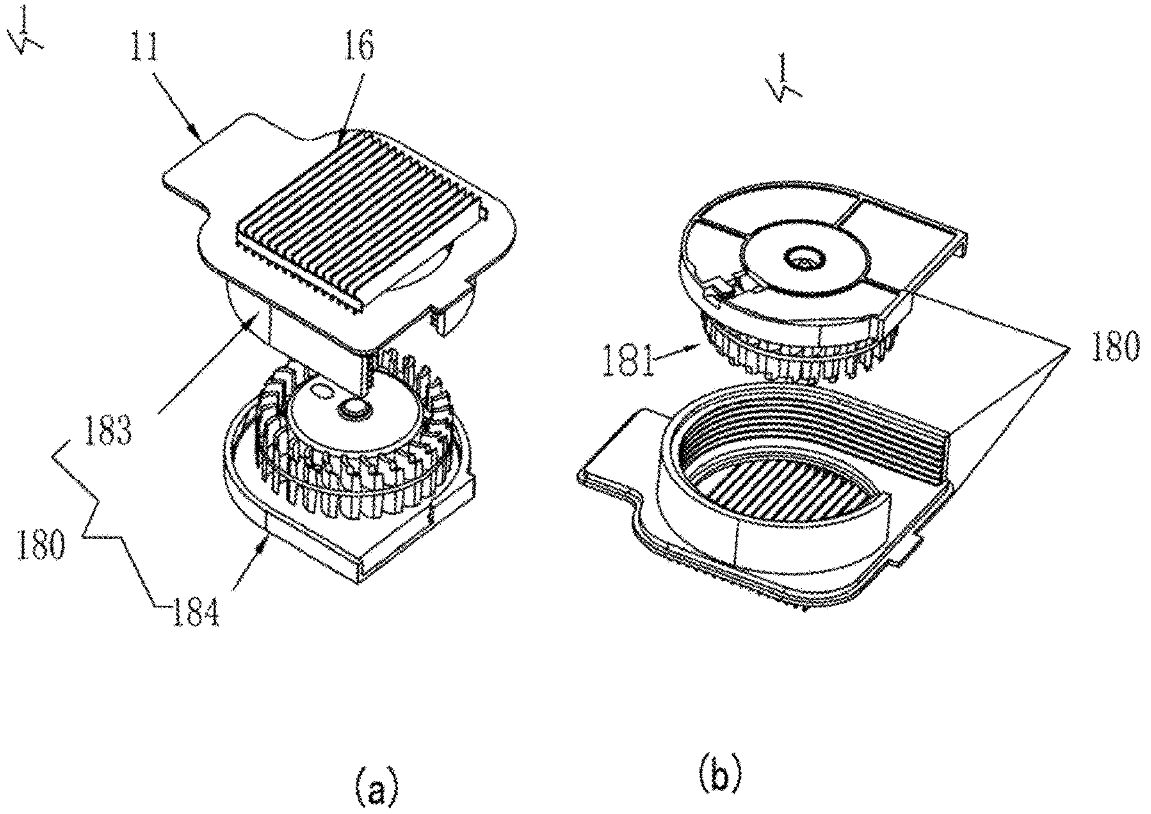
FIG. 14 is partly exploded views of the fan in the thermoelectric cooling assembly of the present invention, where figure (a) and figure (b) illustrates the fan in different directions.

The Vapor Chamber 11 can be a part of the casing 180 of the fan 18. The casing 180 comprises a top cover, a bottom cover 184 and a side frame 183. The inner wall of the side frame 183 can be provided with fins to increase the heat dissipation area. As shown in FIGS. 12-14, the Vapor Chamber 11 serves as the top cover (or the bottom cover) of the fan 18 and is installed on a top (or bottom) opening of the side frame 183; the Vapor Chamber 11 can be set as an annular flat plate with a central through hole as a vent for the fan 18; the heat sink 16 may be provided as a set of parallel heat dissipation fins covering the central through hole. The air flow paths between the heat dissipation fins and the central through hole of the Vapor Chamber 11 and the internal cavity of the fan casing 180 are in an air communication.

Figure 15:
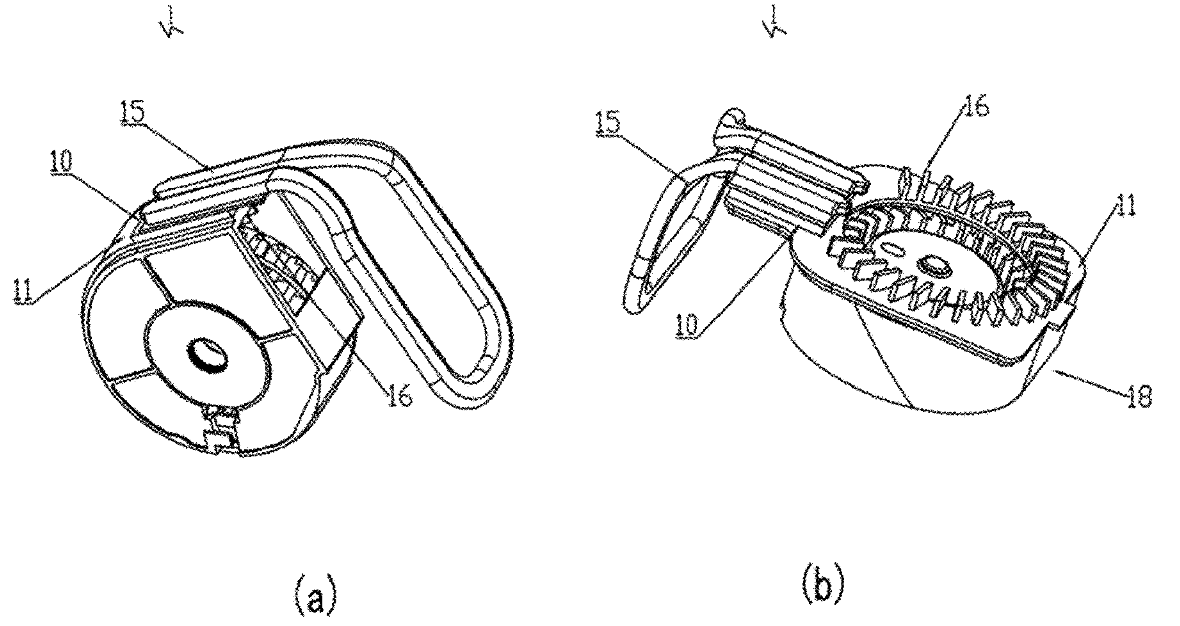
FIG. 15 is perspective views of the thermoelectric cooling assembly in accordance with an alternative embodiment of the present invention, where figure (a) and figure (b) illustrates the thermoelectric cooling assembly in different directions.
Figure 16:
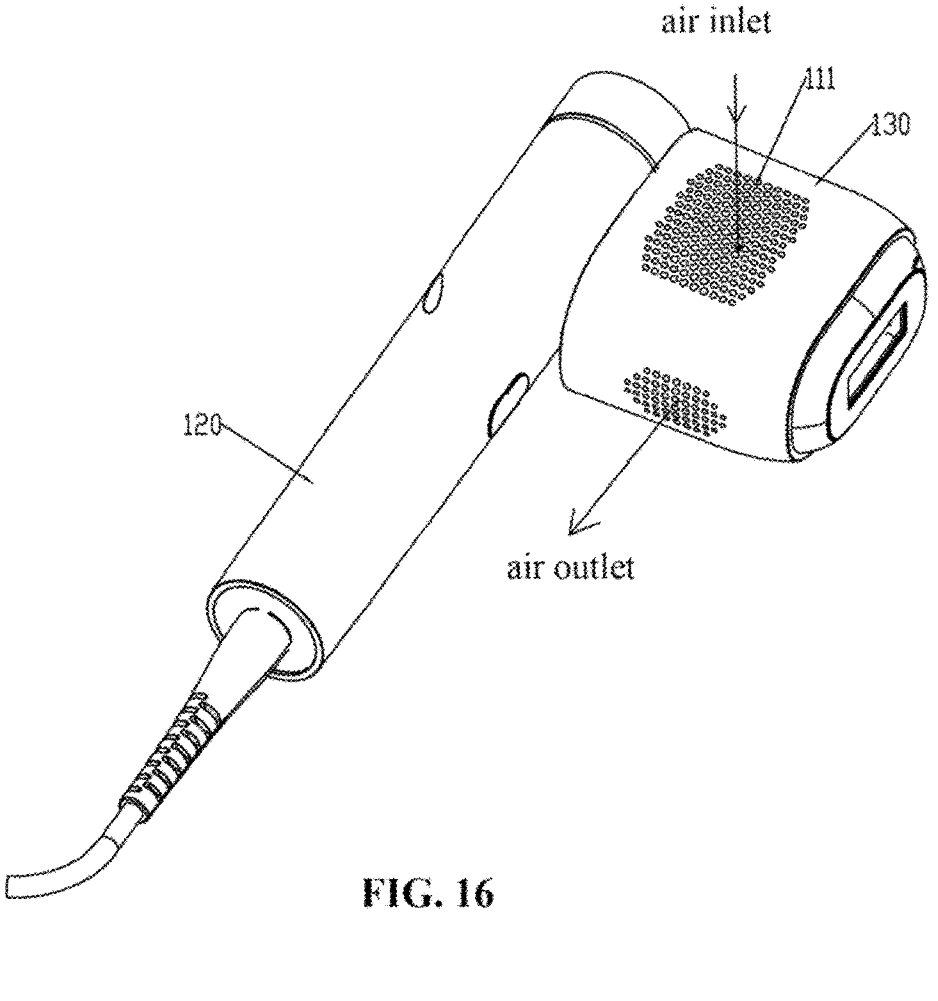
FIG. 16 is a perspective view of a beauty instrument in accordance with a second embodiment of the present invention.
Figure 17:
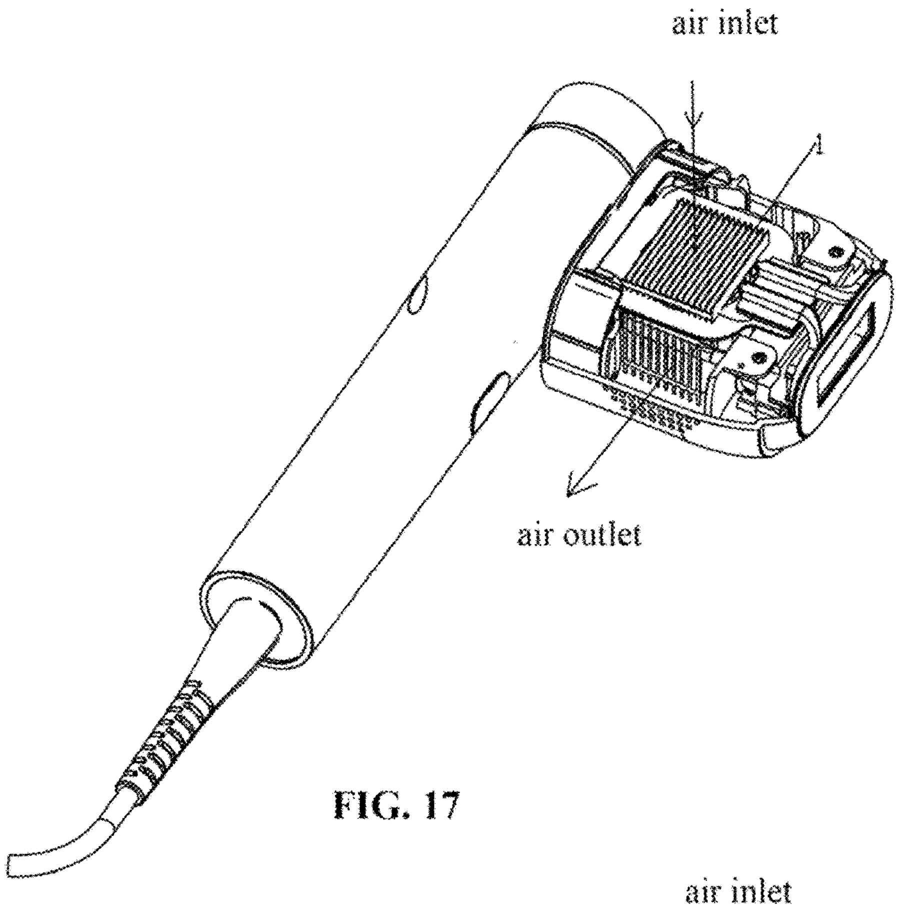
FIG. 17 is a perspective view of the beauty instrument in accordance with the second embodiment of the present invention with the upper shell removed.
Figure 18:
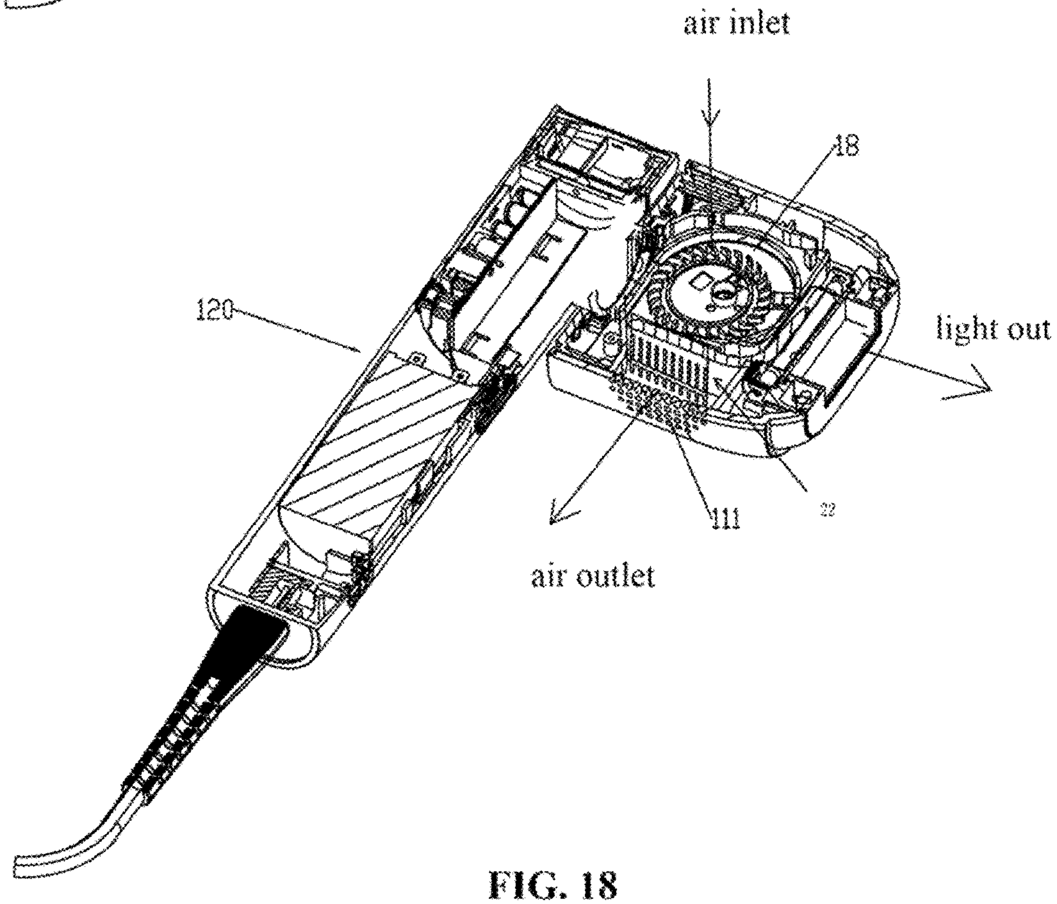
FIG. 18 illustrates an internal structure of the beauty instrument in accordance with the second embodiment of the present invention.
Figure 19:
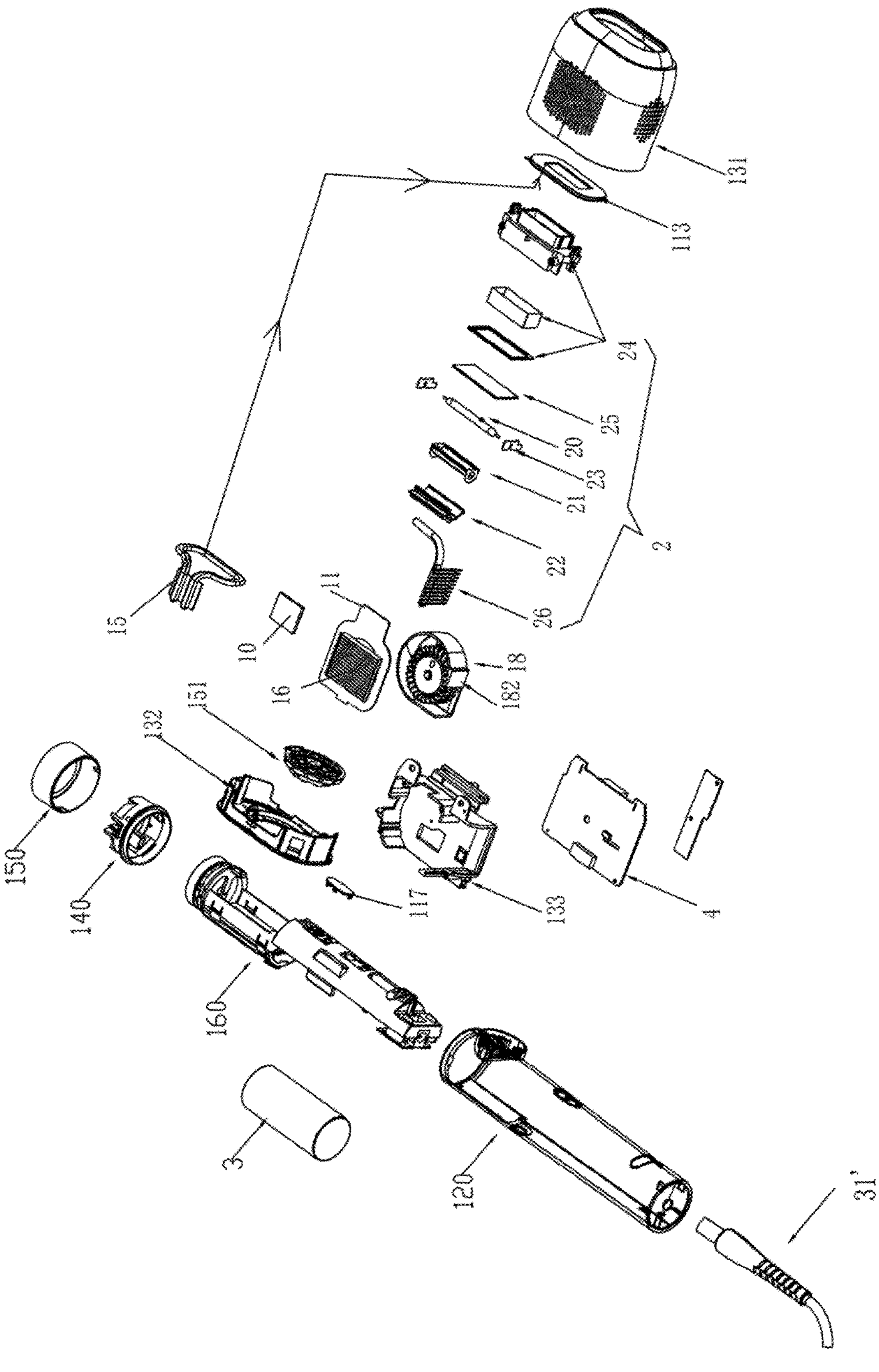
FIG. 19 is an exploded view of the beauty instrument in accordance with the second embodiment of the present invention.
Figure 20:
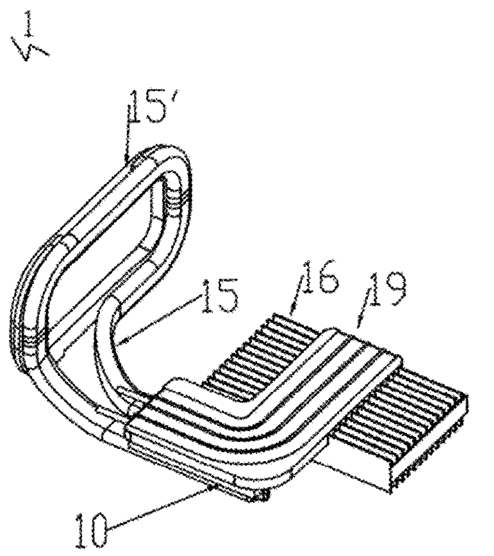
FIG. 20 is a perspective view of the thermoelectric cooling assembly in accordance with the second embodiment of the present invention.
Figure 21:
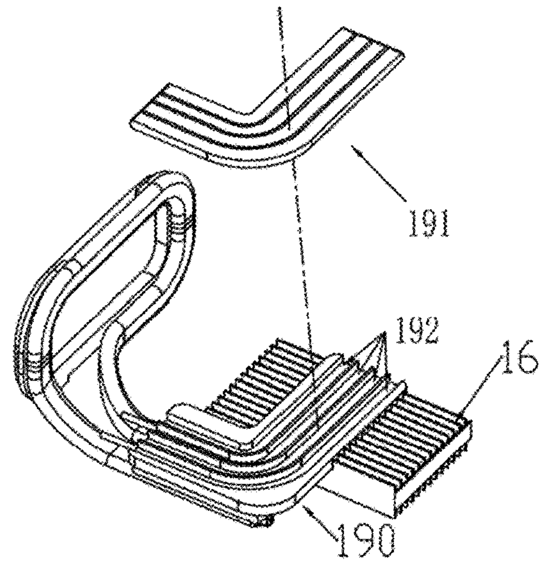
FIG. 21 is a partially exploded view of the thermoelectric cooling assembly in accordance with the second embodiment of the present invention.
Figure 22:
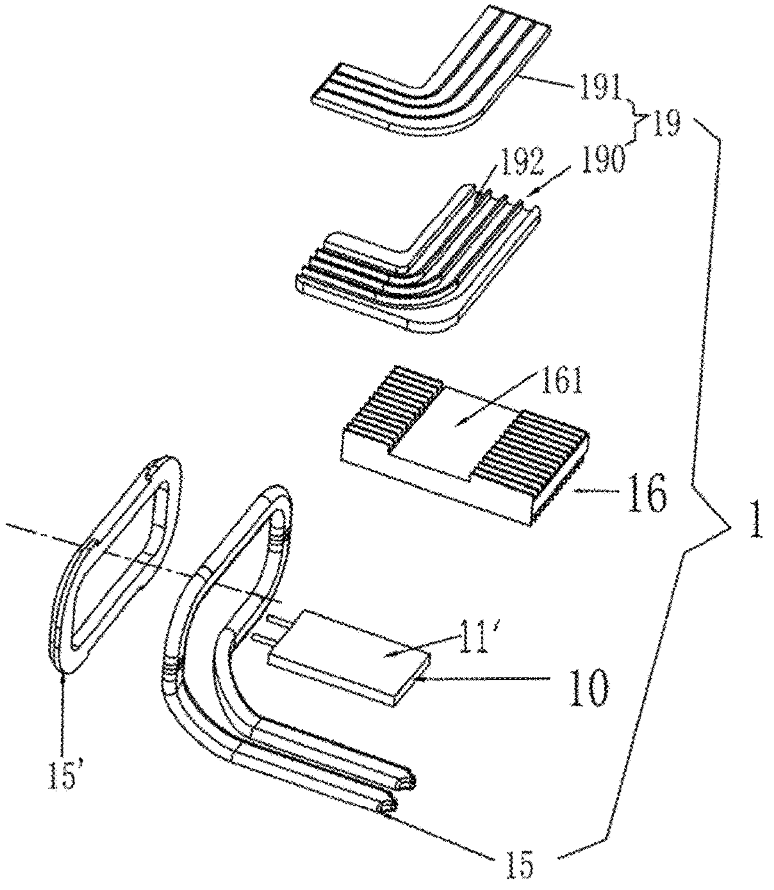
FIG. 22 is an exploded view of the thermoelectric cooling assembly in accordance with the second embodiment of the present invention.

Referring to FIG. 15(*b*), different from as shown in FIGS. 12-14, the heat dissipation fins are arranged along the annular edge of the central through hole of the Vapor Chamber 11, and arranged radially or at a rotation direction.

Referring to FIG. 15(*a*), the VC 11 is used as the side frame around the fan blades, the heat sink 16 can be arranged on the inner wall of the side frame, and the thermoelectric cooler 10 is provided on the outer wall of the side frame.

The thermoelectric cooling assembly 1 of the present invention can also used for heat dissipation of the light source assembly 2. The light source assembly 2 comprises a lamp tube 20 with electrodes 23 at both ends of the lamp tube, and a reflective cover 21 outside the lamp tube. The lamp tube 20 is preferably an IPL lamp tube which generates IPL light wave, or a halogen lamp or other suitable light source. An air flow path for the light source assembly 2 is connected with the air flow path of the fan 18 and is connected with the air flow path in the housing of the beauty instrument 100 to form a heat dissipation air flow path of the light source assembly 2. The fan 18 promotes heat dissipation of the light source assembly 2. A heat transfer member 22 may be provided on back of the reflective cover. For example (but not limited to), the heat transfer member 22 is a set of thermal conductive fins (made of thermally conductive material). One end of the heat transfer member is connected to an outer wall of the reflective cover, and the other end extends to the vent 182 of the fan 18. A plurality of vents 182 may be formed in the casing 180 of the fan 18, specifically in the side frame around the fan blades. As shown in FIG. 13, three vents 182 are provided in the side frame 183, one of which (the first) vent is used for containing the heat transfer member 22 of the reflective cover 21, and connects the air flow path of the fan 18 with the air flow path in the housing of the beauty instrument 100 to form a first air flow path 101 (refer to the arrow line in FIG. 4), which is used for heat dissipation of the heat transfer member 22 and Vapor Chamber 11. At this time, external air enters from the vent (air inlet) 111 in front of the heat sink 16, passes through the heat sink 16 and enters the fan 18 from the central through hole of the Vapor Chamber 11, where the rotating blades cause the airflow to circulate in the cavity inside the fan and flow through the heat transfer member 22 and the Vapor Chamber 11, the heat from the reflective cover 21 and the Vapor Chamber 11 is taken away by air from the fan through another (second) vent 182 in the side shell 183, hot air passes along the air flow path in the housing of the beauty instrument 100 and are discharged from the vent (air outlet) 111 at the end of the housing to outside of the beauty instrument 100 to realize heat dissipation. Another (third) vent 182 in the side shell 180 is in air communication with the inside reflective cover 21 of the lamp tube, and connects the air flow path of the fan 18 and the air flow path in the housing of the beauty instrument to form a second air flow path 102 for heat dissipation of the reflector with 21 and lamp tube 20; where external air enters from the vent 111 facing the heat sink 16, passes through the heat sink 16 and the central through hole of the Vapor Chamber 11, and enters the fan 18, flows out of the fan through another vent (air outlet) 182 in the side shell and enters an inner space of the reflective cover 21, take away the heat of the lamp tube 20 and the reflective cover of the reflector and flows out of the lamp tube, flows along the air flow path in the housing of the beauty instrument, and is discharged from the vent (air outlet) 111 at the end of the housing to the outside of beauty instrument 100.

Figure 5:
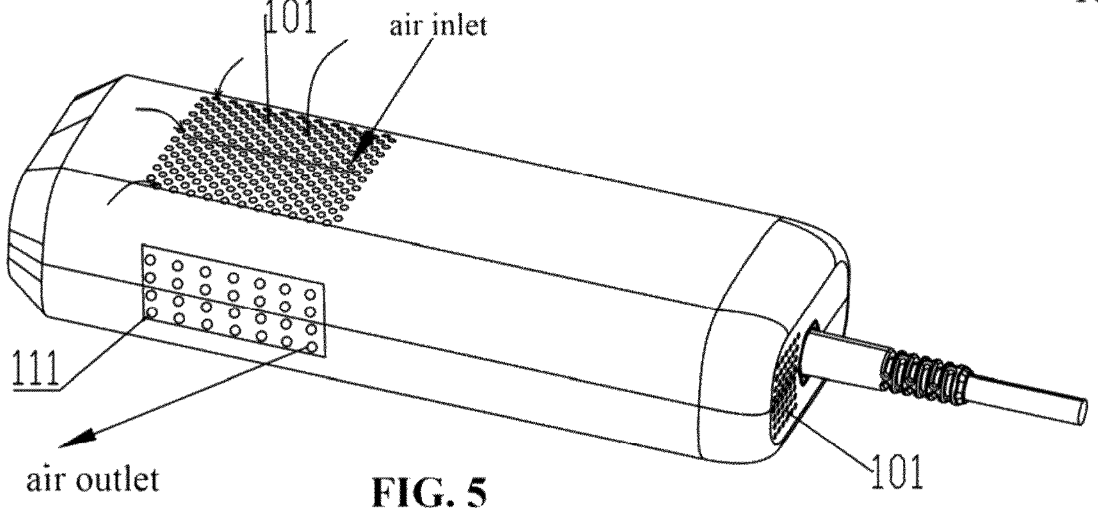
FIG. 5 illustrates air inlet and outlet of the beauty instrument in accordance with another embodiment of the present invention.
Figure 6:
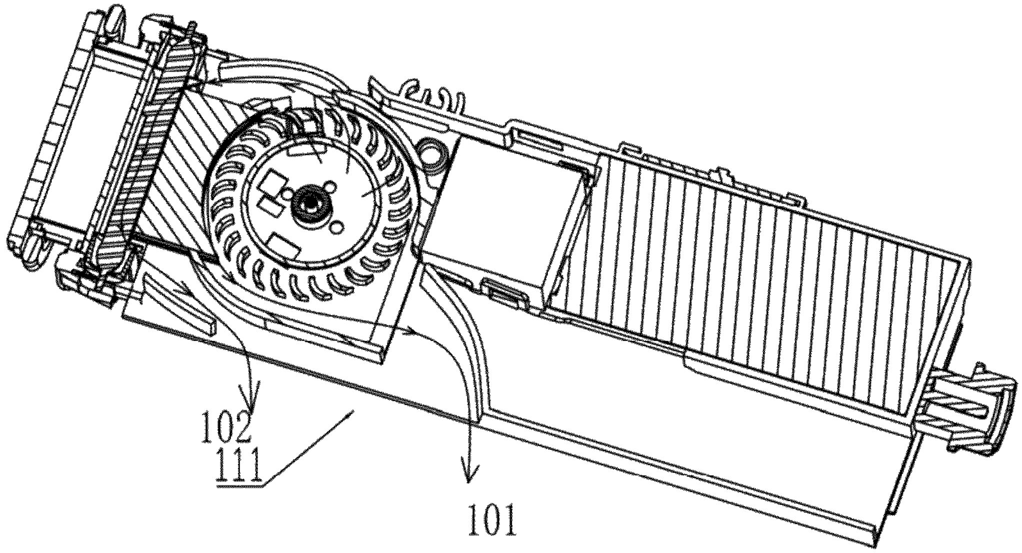
FIG. 6 illustrates an air flow path in the beauty instrument of FIG. 5.
Figure 7:
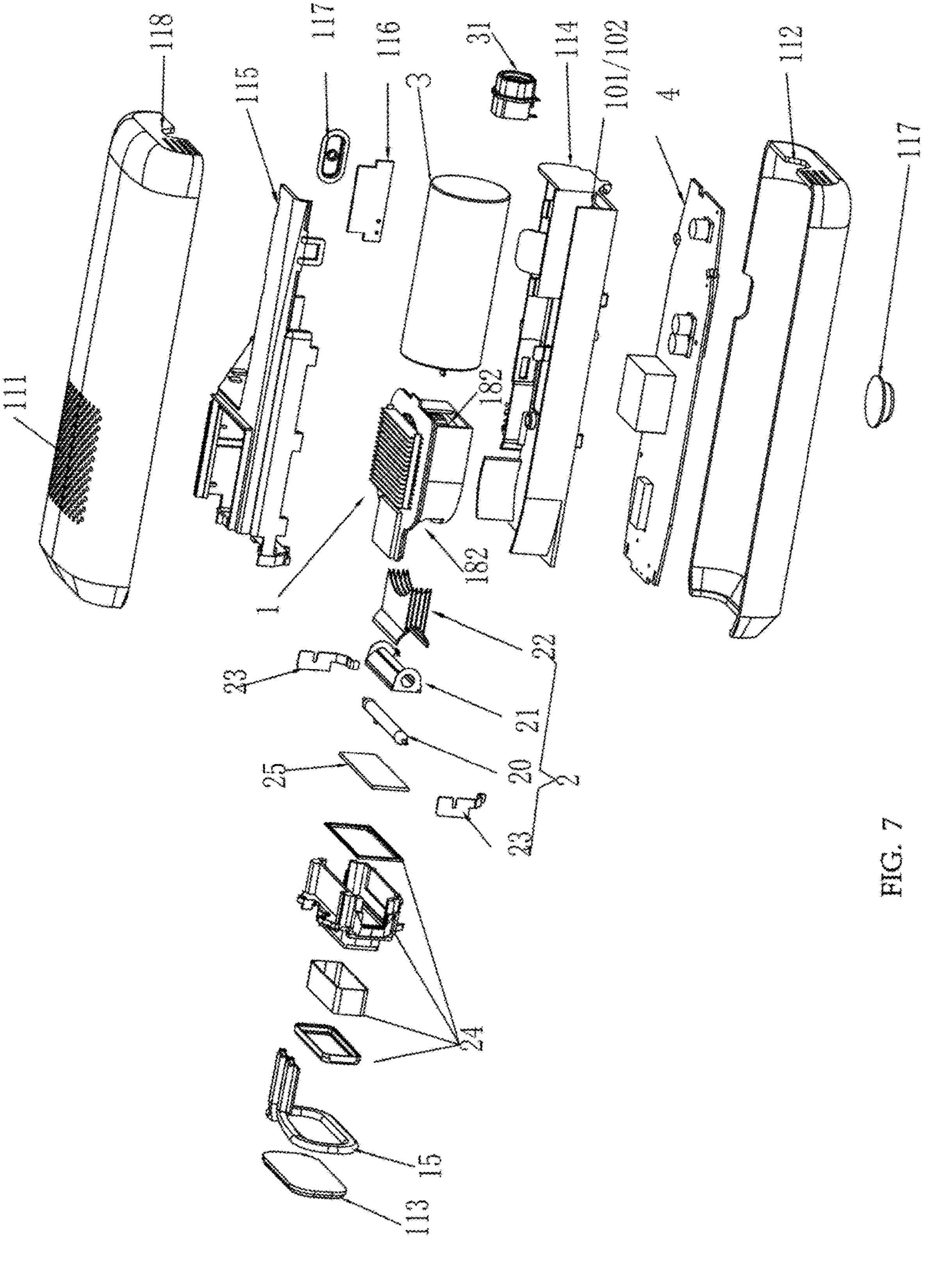
FIG. 7 is an exploded view of the beauty instrument of FIG. 1.
Figure 8:
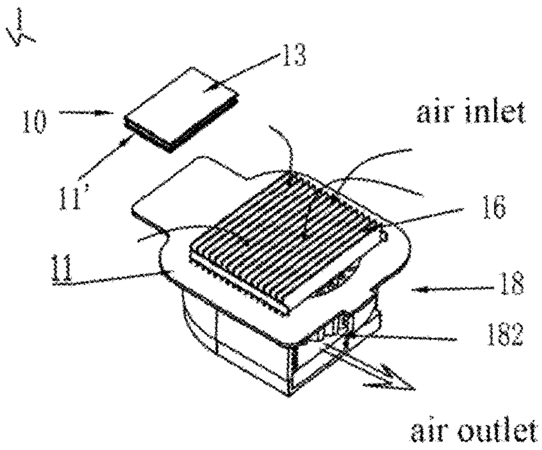
FIG. 8 illustrates a partly exploded view of the thermoelectric cooling assembly in accordance with the first embodiment of the present invention.
Figure 9:
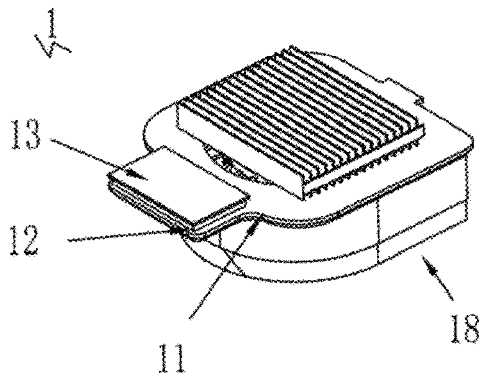
FIG. 9 is a perspective view of the thermoelectric cooling assembly in accordance with the first embodiment of the present invention.
Figure 10:
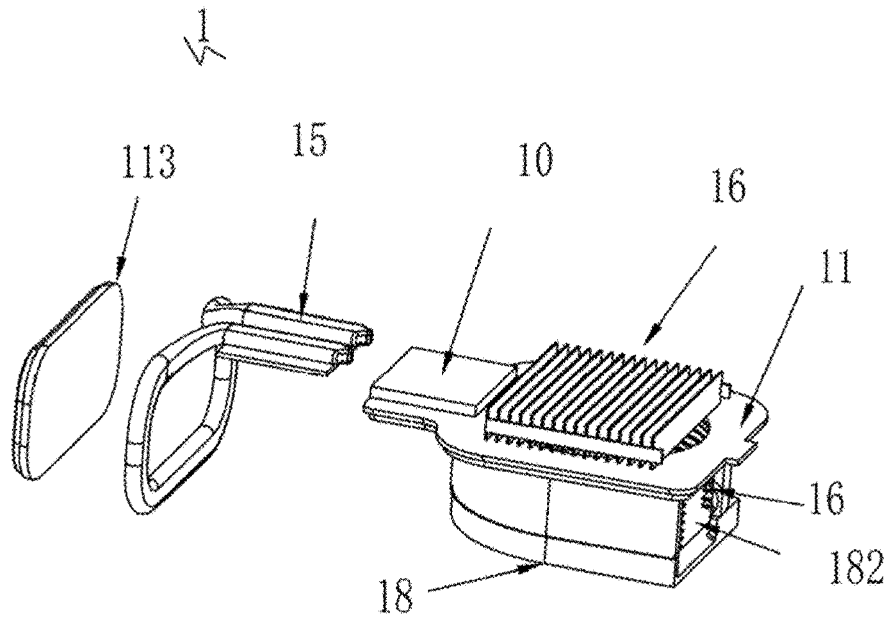
FIG. 10 is a partly exploded view of the thermoelectric cooling assembly connected with a light outlet plate in accordance with the first embodiment of the present invention.
Figure 11:
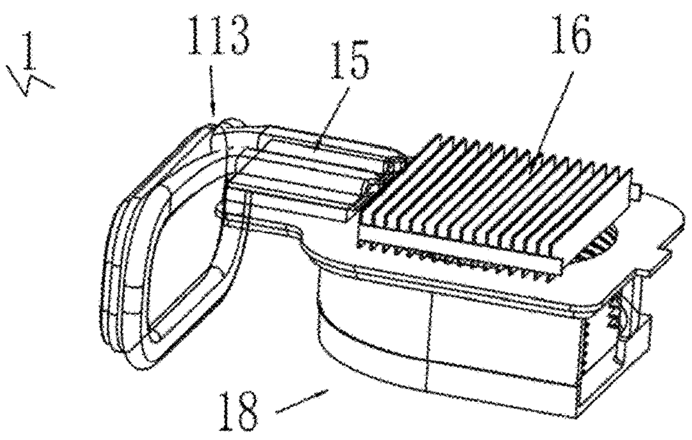
FIG. 11 is a perspective view of the thermoelectric cooling assembly connected with the light outlet plate of the present invention.

The vents 111 in the housing of the beauty instrument 100 can be arranged in different positions and in different forms; for example, in FIGS. 5-6, vents are respectively provided in the bottom or side of the housing, where the vents in the side can serve as air outlets of the first air flow path 101 and the second air flow path 102, the vents 111 in the side of the housing is in air communication with the air flow path in the housing of the beauty instrument 100.

The beauty instrument 100 of the present invention uses the thermoelectric cooling assembly 1 of the above embodiments to cool the light out surface 113 of the beauty instrument head. The fan 18 of the thermoelectric cooling assembly 1 can be used for heat dissipation of the light source assembly 2 at the same time. The beauty instrument can be a hair removal device, a photon rejuvenation device, an import and export beauty device, a RF beauty device, etc., all of which can use the thermoelectric cooling assembly 1 of the above embodiment.

The beauty instrument 100 shown in FIGS. 1-7 in a first embodiment of the present invention has a straight body, and can be used as an IPL photon hair removal instrument. Referring to FIGS. 1-19 together, an embodiment of the present invention relates to a beauty instrument 100, including a housing 110 provided with a plurality of vents 111 as air inlet and air outlet of the beauty instrument. The housing 110 comprises a first shell 112 and a second shell 118, which are interlocked and form a space inside the housing of the beauty instrument. The housing 110 of the beauty instrument is also provided with a first bracket 114 and a second bracket 115 that cooperate with the first shell 112 and the second shell 118 respectively, and a lamp bracket 24 is provided inside the beauty instrument 100; the brackets are used to install the thermoelectric cooling assembly 1, the light source assembly 2, the battery 3 and control circuit board 4 in the housing 110.

A plurality of vents 111 can be disposed at different or the same position of the housing 110 in various forms. For example, the vents 111 are provided in the second shell 118 or the side or end of the housing 110. The space together the brackets inside the housing 110 of the beauty instrument forms an air flow path. The air from the environment enters the inside of the housing 110 of the beauty instrument 100 through the vents 111, takes away the heat and is discharged out of the beauty instrument 100 through the vents 111 at the same or different positions. Vents 111 in the housing of the beauty instrument are used for air inlet and outlet in air communication with the space inside the housing of the beauty instrument to form the air flow path (the line with arrows in FIGS. 4-6) for heat dissipation. A front end of the head of the beauty instrument 100 has a light out surface 113. The light out surface 113 can be in direct contact with the skin. The light generated by the light source assembly 2 is transmitted through the light out surface 113 to perform beauty treatment on the skin.

The light source assembly 2 is installed in the head of the beauty instrument through the lamp bracket 24. A light outlet channel and a light outlet window are formed in the lamp bracket 24 for transmitting the light generated by the light source assembly 2. The light out surface 113 is installed at the light outlet window, the lamp tube 20 is installed in the rear of the lamp bracket 24 by the reflective cover 21, and is located behind the light outlet channel. A filter 25 is provided in the light outlet direction of the light source assembly. The heat transfer member 22 fitted on back of the reflective cover extends backward to the vent 182 of the fan 18. An air flow path can be provided in the lamp bracket 24 if desired, and is connected with the air flow path inside the reflective cover to facilitate cooling and heat dissipation.

Front end of the first bracket 114 and the second bracket 115 inside the housing of the beauty instrument forms a fan accommodation cavity, corresponding to which the thermoelectric cooling assembly 1 is installed. The front end of the second bracket 115 forms an opening, facing vents 111 in the second shell 118. The heat sink 16 on the Vapor Chamber 11 is located in the opening and faces the vents 111 in the second shell 118 accordingly. The thermoelectric cooler 10 is installed on the platform of the Vapor Chamber 11. The heat transfer component (such as heat pipe) 15, is supported by the lamp bracket 24. An annular front section of the heat transfer component and the light out surface 113 are contacted and connected for rapid heat transfer, and a rear section thereof in the form of parallel straight tubes covers the cold side 13 of the thermoelectric cooler 10 and is in close contact for rapid heat transfer. The fan 18 is installed in the fan accommodating cavity, the front vent 182 in the side frame 183 corresponds to the heat transfer member 22, and a rear vent 182 is connected to the air flow path formed after the first bracket 114 and second bracket 115 are buckled. Refer to the air inlet and outlet shown in FIG. 8 for the air flow in the fan.

The rear section of the first bracket 114 and the second bracket 115 inside the housing of the beauty instrument forms a battery accommodating cavity for mounting the battery 3. The battery 3 is generally a rechargeable battery or a capacitor battery. The battery 3 is connected with a power connector 31 for connecting an external power source to charge the battery. The power connector 31 is connected with the control circuit board 4 can be used to directly connected with an external power without the battery 3. The power connector 31 extends outside from a port in the housing 110.

Beside the battery accommodating cavity, the interior of the first bracket 114 and the second bracket 115 is defined with an air flow path 101/102. The air flow path 101/102 is in air communication with the air flow path of the fan 18, is in air communication with the air flow path in the reflective cover 21, and is in air communication with the vents (air inlet and outlet) 111 in the housing 110 to form an air flow path inside the housing of the beauty instrument.

The control circuit board 4 is installed in the cavity formed by the first bracket 114 and the first shell 112, and the control circuit board 4 is protected by the first bracket 114 and the first shell 112. The housing 110 is also equipped with a switch button 117 and a corresponding internal switch circuit board 116 for on/off control, etc. The switch circuit board 116 is electrically connected to the control circuit board 4.

Referring to FIGS. 16-19, the thermoelectric cooling assembly 1 of the aforementioned embodiment is applied to an L-shaped beauty instrument in a second embodiment of the present invention. The function and structure are the same or similar to the straight beauty instrument 100 as shown in FIGS. 1-7. According to the overall shape of the L-shaped beauty instrument, the size, shape and position of the housing, brackets, battery 3, light source assembly 2, thermoelectric cooling assembly 1 and control circuit board 4 are adaptively configured. The L-shaped beauty instrument comprises a handle 120 and a lamp head 130. The lamp head 130 is rotatably connected to a top of the handle 120 by a rotating connection structure which comprises a knob 150, a knob seat 140 and a rotating pressure plate 151 at the top of the handle 120. The rotating connection structure between the lamp head 130 and the handle 120 and the structure of the handle can adopt the structure in the prior art. The tail of the handle has a DC line 31' for providing external power to the control circuit board 4, and a handle bracket 160 is provided inside the handle 120 to install the battery 3 electrically connected with the control circuit board 4. The side cavity at the top of the handle bracket 160 is connected with the inside of the lamp head 130, and is used for the rotatably installing the lamp head housing. The lamp head housing comprises a front casing 131 and a front base 132. The lamp head 130 is rotatably connected by the front base 132 cooperating with the knob 150, the knob seat 140 and the rotating pressure plate 151. The inner bracket 133 in the lamp head 130 is installed on the front base 132 and cooperates with the front casing 131. The thermoelectric cooling assembly 1 is installed at one side and the control circuit board 4 is installed on the other side of the inner bracket for protecting the control circuit board 4. A front end of the lamp head 130 has a light out surface 113, which can be a transparent plate (such as a transparent crystal) or in an annular shape, an annular thermoelectric cooler, or a thermoelectric cooler with a transparent substrate of cold side. A lamp bracket 24 is arranged in the lamp holder 130, which has a structure similar to the embodiment as shown in FIGS. 1-7. The light source assembly 2 is installed in the lamb bracket 24. A heat pipe and heat sink assembly 26 are provided to connect the heat transfer member 22 fitted on back of the reflective cover 21, extends to the vent 182 of the fan 18, and faces the vents defined in the front case 131. In this embodiment, the thermoelectric cooling assembly 1 is used to cool the light out surface 113 and dissipate heat from the light source assembly 2.

In the present invention, a thermoelectric cooler 10 is provided on the VC (Vapor Chamber) 11, and the cold side 13 of the thermoelectric cooler 10 is connected to the light out surface 113 of the beauty instrument by a heat transfer component (heat pipe) 15, to quickly cooling the light out surface 113, thus the light out surface 113 can provide a cold compress or cooling effect on the skin. Heat sinks 16 are provided on the Vapor Chamber 11 for heat dissipation. Furthermore, the Vapor Chamber 11 is set on the fan 18 as a top or bottom cover or side frame, in such way to improve the heat dissipation efficiency.

Figure 23:
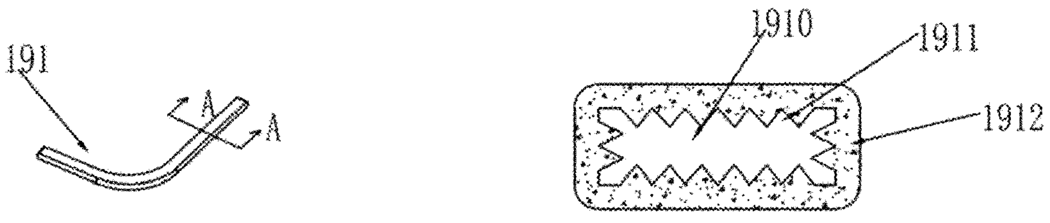
FIG. 23 illustrates an Aluminum VC or an Aluminum Heat Pipe of the thermoelectric cooling assembly in accordance with an embodiment of the present invention, where figure (a) is a perspective view of a single Aluminum VC or Aluminum Heat Pipe, and figure (b) is a cross-sectional view along A-A of figure (a)

Referring to FIGS. 20-23, the thermoelectric cooling assembly 1 in accordance with a second embodiment of the present invention is mainly used for cooling the light out surface 113 of the beauty instrument (refer to the previous embodiment) to achieve a cold compress effect on the skin. The thermoelectric cooling assembly 1 comprises a thermoelectric cooler 10. The thermoelectric cooler 10 (refer to the previous embodiment) comprises semiconductors 12 in the middle and a hot side 11' and a cold side 13. In a specific embodiment, the thermoelectric cooler 10 (specifically the cold side 13) can be directly used as the light out surface 113, or used to cool the light out surface 113. When the thermoelectric cooler 10 is directly used as a light out surface, the cold side 13 is a transparent substrate (such as a transparent crystal), or the thermoelectric cooler 10 has an annular shape. When the thermoelectric cooler 10 is used to cool the light out surface 113, the cold side 13 of the thermoelectric cooler 10 contacts the light out surface 113, for example, is arranged around the light out surface. Alternatively, the cold side 13 and the light out surface 113 of the thermoelectric cooler 10 are in contact with the light out surface 113 through a heat transfer component. A heat transfer component 15 can quickly transfer the heat of the light out surface to the thermoelectric cooler 10 to obtain a cooling effect of the light out surface. The heat transfer component may be a thermally conductor which may be made of metal materials such as (not limited to) copper/aluminum tubes or copper/aluminum plates, or made of other thermally conductive materials such as silicone grease/silicon wafers/elastic or soft thermally conductive materials. The heat transfer component 15 may also be a heat pipe or VC (Vapor Chamber) or super heat conductive pipe (Aluminum Heat Pipe) or super heat conductive plate (Aluminum Vapor Chamber) or others for a rapid heat transfer. The super heat pipe or super heat plate is preferably an aluminum super heat pipe (Aluminum Heat Pipe)/aluminum super heat plate (Aluminum Vapor Chamber). Aluminum Heat Pipe or Aluminum Vapor Chamber (ALVC), is based on gas-liquid phase change to quickly transfer heat. Referring to FIG. 23, compared with general heat pipes or Vapor Chambers, micro-grooves, micro-teeth or micro-hole channels can be formed in the inner wall surface of the Aluminum Heat Pipe/Aluminum Vapor Chamber through aluminum processing and molding processes as capillary structures inside Aluminum Heat Pipe/Aluminum Vapor Chamber. It may be not need to add copper powder inside Aluminum Heat Pipe/Aluminum Vapor Chamber, while can add aluminum powder or aluminum-silicon powder or aluminum meshes therein, and refrigerant is contained in the sealed Aluminum Heat Pipe/Aluminum Vapor Chamber. A first heat transfer component 15 is connected between the thermoelectric cooler (cold side) and the light out surface, and can be configured an adaptive shape according to the shape of the thermoelectric cooler 10, especially the shape of the cold side 13, the shape of the light out surface 113, and the principle of rapid heat dissipation. In one embodiment, the heat transfer component 15 is a copper tube, an Aluminum Heat Pipe/Aluminum Vapor Chamber, a heat pipe, or a VC.

According to the shape of the light out surface 113 and the expected cooling effect, the section of the heat transfer component 15 that contacts the light out surface 113 can be designed to be annular and in direct and close contact with the periphery of the light out surface to quickly transfer heat the light out surface 113; alternatively, a second heat transfer component 15' is further provided between the light out surface 113 and the first heat transfer component 15 for contact heat transfer. The heat transfer component 15' may be a copper tube or Aluminum heat pipe or ALVC or a heat pipe or VC. It can be set in an annular shape and is closely connected to the periphery of the light out surface 113 and the annular section of the first heat transfer component 15 for rapid heat transfer. According to the shape of the thermoelectric cooler 10 or the cold side 13, the heat transfer component 15 that contacts the thermoelectric cooler 10 can be designed as follows: the ends are bent from an annular shape and extend a predetermined length, are placed on the cold side 13 of the thermoelectric cooler and tightly contact the cold side 13.

The thermoelectric cooling assembly 1 is this embodiment comprises the thermoelectric cooler 10, the heat transfer assembly 19 and a heat sink 16. The heat generated by the hot side 11' of the thermoelectric cooler 10 is discharged through the air flow paths in the housing of the beauty instrument. Specifically, the hot side 11' of the thermoelectric cooler 10 dissipate heat through the heat transfer assembly 19 and the heat sink 16 which is located in the air flow path of the beauty instrument. The heat transfer assembly 19 comprises a thermal conductive plate 190 and several Aluminum Vapor Chamber (ALVC) 191. Each ALVC 191 has a single channel 1910 therein through a length thereof. The hot side 11' of the thermoelectric cooler is disposed on an outer wall of the thermal conductive plate 190, or the outer wall of the thermal conductive plate 190 directly serves as the hot side 11' of the thermoelectric cooler 10, where the thermoelectric legs are fixed on the outer wall of the thermal conductive plate 190. One side of the outer wall of the thermal conductive plate 190 is provided with the thermoelectric cooler 10, and the other side is provided with one or more grooves 192. Each groove 192 is adapted to a single Aluminum Heat Pipe/ALVC 191. A single Aluminum Heat Pipe/ALVC 191 is located in one groove 192. The Aluminum Heat Pipe/ALVC 191 and the groove 192 are closely contacted each other for rapid heat transfer, and can be riveted or welded together.

With reference to FIG. 23, micro grooves or micro teeth or micropores are formed in the inner wall surface of the Aluminum Heat Pipe/ALVC through an aluminum processing and molding process and thus capillary action can be generated in the Aluminum Heat Pipe/ALVC. As shown in FIG. 23(*b*), when the Aluminum Heat Pipe/ALVC is extruded from aluminum, a single channel 1910 is formed in the Aluminum Heat Pipe/ALVC, and more than two fine bone-shaped micro grooves 1911 are formed on the inner wall of the Aluminum Heat Pipe/ALVC. A large number of micropores 1912 are formed inside the wall material of the Aluminum Heat Pipe/ALVC. After the aluminum material is formed into a tube or chamber shape, refrigerant, aluminum powder or aluminum silicon powder can be added therein. Aluminum meshes can also be added in the tube or chamber, and the ends of the Aluminum Heat Pipe/ALVC are sintered and sealed after vacuuming. The Aluminum Heat Pipe/ALVC has super thermal conductivity accordingly. Preferably, each Aluminum Heat Pipe/ALVC has a single channel 1910, which will cause the advantages that: the Aluminum Heat Pipe/ALVC can be performed plane bending or special-shaped 3D bending, or configured to be various shapes if desired, therefore, the influence of gravity direction can be reduced, and multiple Aluminum Heat Pipes/ALVC can be staggered and combined longitudinally without the influence of gravity direction. In the example shown in FIG. 23(*a*), the Aluminum Heat Pipe/ALVC 191 is bent into an L shape. Correspondingly, the groove 192 in the heat conductive plate 190 is also L-shaped, and the Aluminum Heat Pipe/ALVC 191 is just embedded in it. In the groove 192, an L-shaped heat transfer assembly 19 is formed as a whole. One end of the L-shape is placed on the hot side 11' of the thermoelectric cooler 10 for close contact and rapid heat transfer, and the other end of the L-shape is installed in the heat sink 16. The heat from the hot side 11' of the thermoelectric cooler 10 is quickly transferred to the heat sink 16 by the heat transfer assembly 19 for heat dissipation.

The thermoelectric cooler 10 is arranged on one side of the heat conductive plate 190, and the hot side 11' of the thermoelectric cooler is mounted on the outer wall of the heat conductive plate 190, so that the heat from the hot side is directly transferred to the heat conductive plate 190; or, the hot side 11' is installed on the outer wall of the thermal conductive plate 190 through a heat transfer member, and the heat from the hot side 11' is quickly transferred to the thermal conductive plate 190 through the heat transfer member; or, the thermoelectric legs of thermoelectric cooler are fixed (e.g. by welding) on the outer wall of the thermal conductive plate 190 so that the outer wall of the thermoelectric cooler serves as the hot side. The thermally conductive plate 190 may be made of thermally conductive materials such as (not limited to) metal materials such as (not limited to) copper/aluminum or other thermally conductive materials such as silicone grease/silicon wafers/elastic or soft thermally conductive materials. Preferably, the thermally conductive plate 190 is made of thermally conductive material such as copper/aluminum.

The heat sink 16 is provided on the heat conductive plate 190 to increase the heat dissipation area. Preferably, the heat sink 16 is located behind the vents 111 of the beauty instrument (referring to FIGS. 16 and 27-28 together). The heat sink 16 comprises one or more sets of heat fins, and the position, quantity and arrangement of the heat sink can be set according to the internal space of the beauty instrument. One or more sets of heat fins are integrally formed or fixed by welding or riveting or other fastening mechanisms to form the heat sink 16 of an integral structure; alternatively, one or more sets of fins are provided on a thermally conductive plate to form an integral structure. A groove 161 may be formed on the top of the heat sink 16 for receiving one end of the heat transfer assembly 19, and the contact area between the groove 161 and the end of the heat transfer assembly 19 can be increased by riveting/welding to obtain rapid heat transfer.

Figure 28:
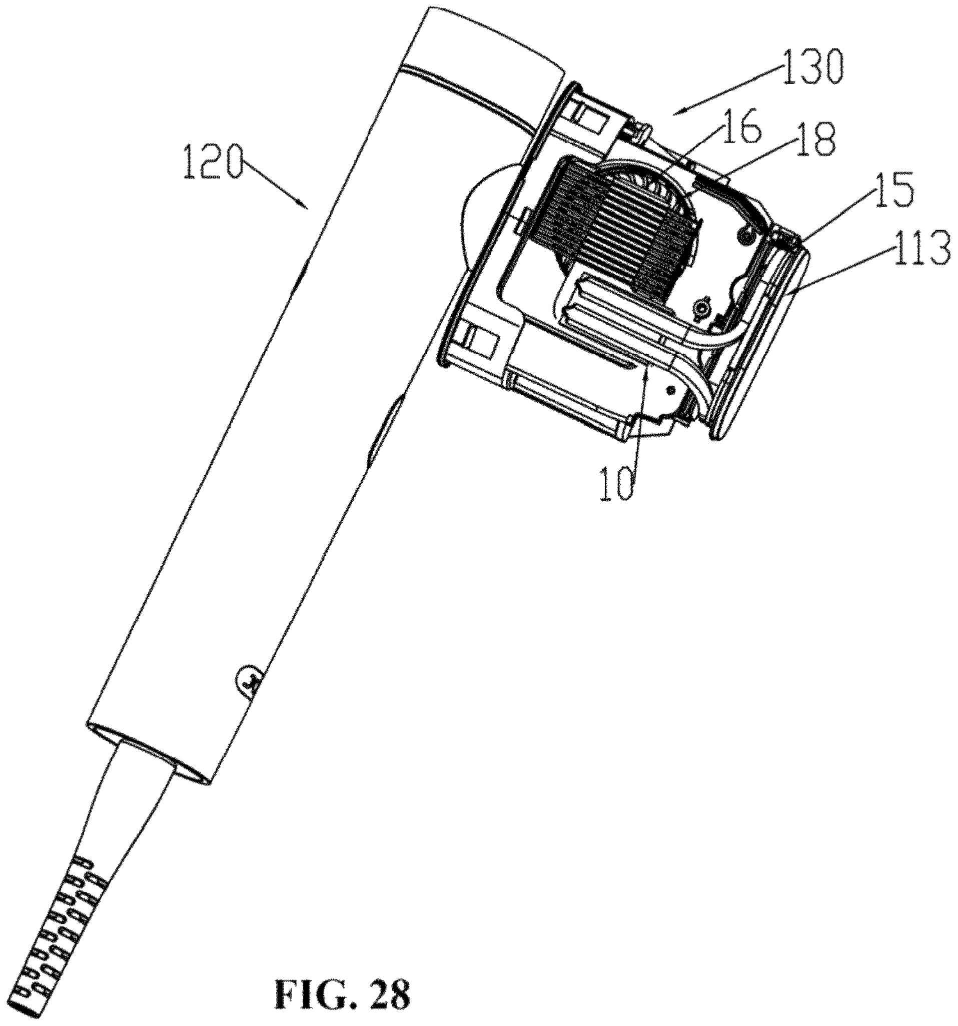
FIG. 28 is a perspective view of the beauty instrument with a front casing removed in accordance with a fourth embodiment of the present invention.

In other embodiments, the heat transfer assembly 19 can also be placed directly on the heat sink 16, or the heat transfer assembly 19 is connected to the heat conductive plate of the heat sink 16 (refer to FIG. 28).

Figure 24:
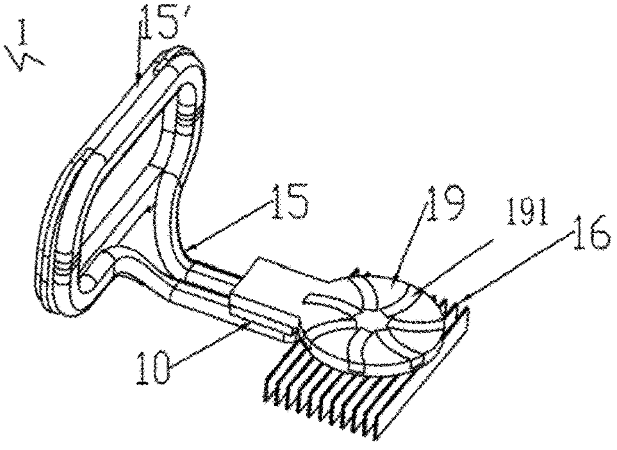
FIG. 24 is a perspective view of the thermoelectric cooling assembly in accordance with a third embodiment of the present invention.
Figure 25:
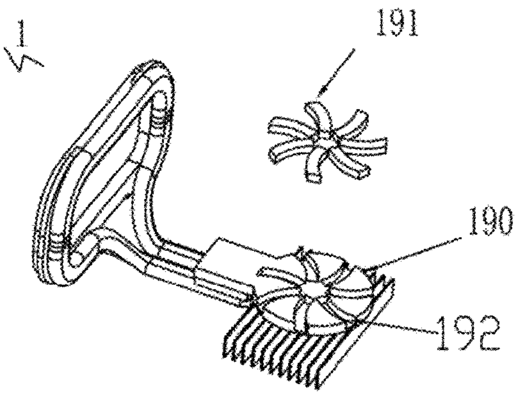
FIG. 25 is a partially exploded view of the thermoelectric cooling assembly in accordance with the third embodiment of the present invention.
Figure 26:
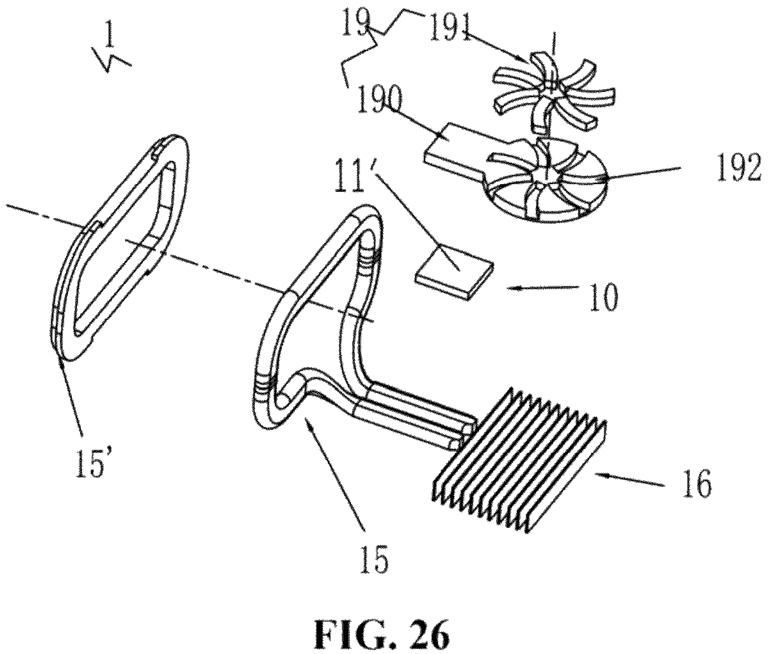
FIG. 26 is an exploded view of the thermoelectric cooling assembly in accordance with the third embodiment of the present invention.

Referring to FIGS. 24-26, the third embodiment of the thermoelectric cooling assembly 1 is mainly used for cooling the light out surface 113 of the beauty instrument (refer to the previous embodiment) to achieve a cold compress effect on the skin. The thermoelectric cooling assembly 1 comprises a thermoelectric cooler 10, a first heat transfer component 15, a second heat transfer component 15', a heat sink 16 and a heat transfer assembly 19. The structures of the first heat transfer component 15, the second heat transfer component 15', and the heat sink 16 are the same as or similar to the second embodiment of the above-mentioned thermoelectric cooling assembly 1. The heat transfer assembly 19 comprises a thermal conductive plate 190 and several Aluminum Heat Pipes/ALVCS 191. Each Aluminum Heat Pipe/ALVC 191 has a single channel 1910 therein through a length thereof. The hot side 11' of the thermoelectric cooler is disposed on the outer wall of the thermal conductive plate 190, or the thermal conductive plate 190 directly serves as the hot side 11' of the thermoelectric cooler 10. One side of the outer wall of the thermal conductive plate 190 is provided with the thermoelectric cooler 10, and the other side is provided with a plurality of grooves 192. The plurality of grooves 192 are adapted to a plurality of Aluminum Heat Pipes/ALVCs 191. The Aluminum Heat Pipes/ALVCs are 191 are located in the grooves 192 correspondingly. The groove 192 is in close contact with the Aluminum Heat Pipe/ALVC 191 by riveting or welding, to increase the contact area therebetween for rapid heat transfer. In this embodiment, the thermal conductive plate 190 comprises a circular (not limited to circular) area and a platform extending on one side, on which the thermoelectric cooler 10 is disposed. Grooves 190 are provided in the circular area extending from a center to the periphery of the circle, and are evenly spaced in the circular area. One Aluminum Heat Pipe/ALVC 191 is placed in each groove 190. The grooves 190 and the Aluminum Heat Pipe/ALVC 191 can be configured to a certain curvature or radian. In a non-limiting example, after installation, multiple Aluminum Heat Pipes/ALVCs 191 form a radial arrangement along the radius or approximately along the radius direction, which can overcome the influence of the gravity direction. In other embodiments, multiple Aluminum Heat Pipes/ALVCs 191 can be arranged in a staggered longitudinal pattern to overcome the influence of the gravity direction.

The same as the previous embodiment, the Aluminum Heat Pipe/ALVC 191 preferably adopts a single channel. Micro grooves, micro teeth or micro holes are formed on the inner wall surface of the Aluminum Heat Pipe/ALVC through an aluminum processing and molding process, and refrigerant is contained inside, and aluminum powder or aluminum silicon powder and aluminum mesh can also be added inside.

The thermoelectric cooler 10 is arranged on a platform on one side of the heat conductive plate 190, and the hot side 11' of the thermoelectric cooler is mounted on the outer wall of the heat conductive plate 190, so that the heat from the hot side is directly transferred to the heat conductive plate 190; or, the hot side 11' of the thermoelectric cooler 10 is installed on the outer wall of the thermal conductive plate 190 through a heat transfer member, and the heat from the hot side 11' is quickly conducted to the thermal conductive plate 190 through the heat transfer member; or, the thermal conductive plate 190 serves as the hot side. Preferably, the thermally conductive plate 190 is made of thermally conductive material such as a copper/aluminum plate.

The heat sink 16 is provided on the thermal conductive plate 190 to increase the heat dissipation area. In non-limiting examples, the circular area of the heat transfer assembly 19 can be directly disposed on the top of the heat sink 16, or fixed to the top of the heat sink 16 by welding or riveting for quickly transfer heat. A platform extending form one side of the thermal conductive plate 190, and the thermoelectric cooler 10 is disposed on the platform.

Figure 27:
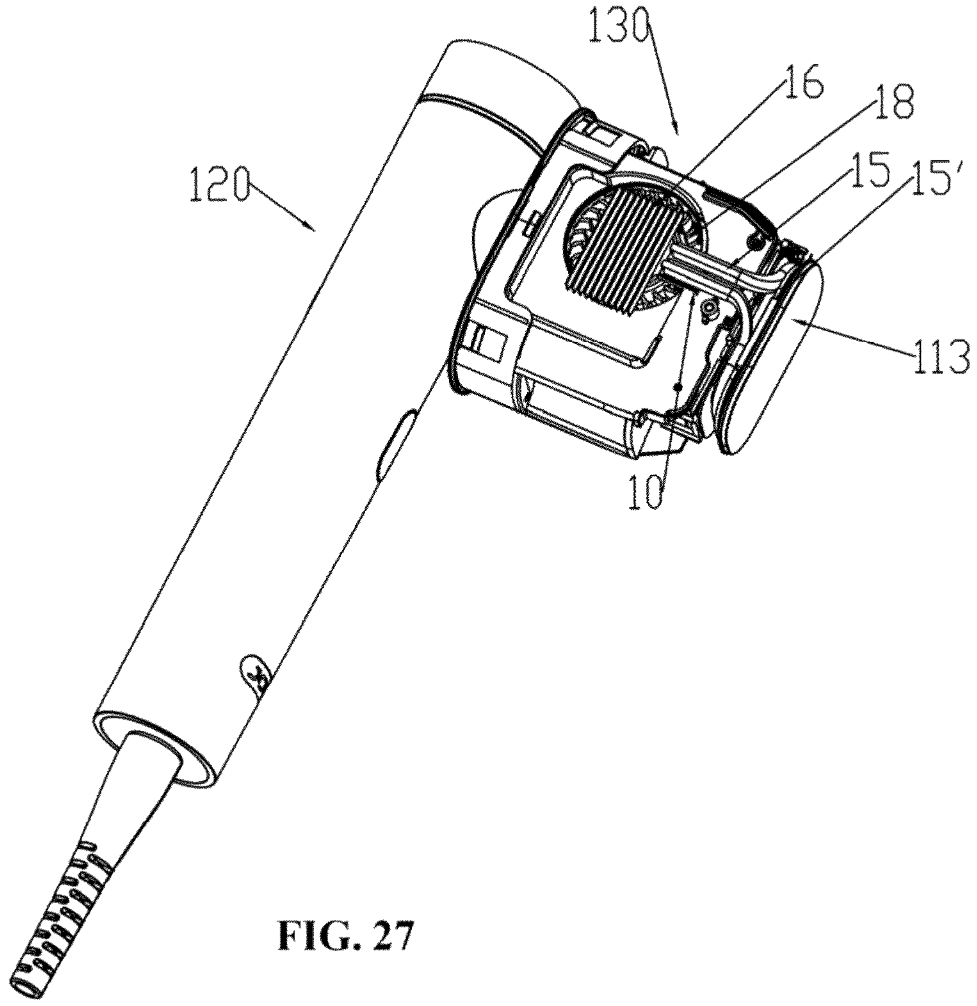
FIG. 27 is a perspective view of the beauty instrument with a front casing removed in accordance with a third embodiment of the present invention.

Referring to FIG. 27, the thermoelectric cooling assembly 1 of the above-mentioned third embodiment is applied to a beauty instrument, for example, to the beauty instrument with the shape as shown in FIGS. 16-19. The other structural parts of the beauty instrument are the same as the embodiment above as shown in FIGS. 16-19. The heat transfer assembly 19 is disposed at the vent of the top of the fan 18. Specifically, the circular area of the thermal conductive plate 190 is covered on the vent on the top of the fan. The Aluminum Vapor Chambers or Aluminum Heat Pipes 191 are installed on the thermal conductive plate toward the fan 18, and the heat sink 16 is located on the outside of the fan. The vents 111 in the side of the front casing 131, the heat transfer assembly 19, the fan 18, and the heat sink 16 are all located in the air flow path in the housing of the beauty instrument. Cold air is input from the vents (air inlet) 111 of the housing of the beauty instrument, heat is taken away from the air flow path and then discharged to the outside of the beauty instrument through another vents (air outlet) 111.

The thermoelectric cooler 10 is provided on the platform of the heat conductive plate 190, and the cold side of the thermoelectric cooler 10 and the light out surface 113 are connected by the first heat transfer component 15 and the second heat transfer component 15' for cold quickly, thus the light out surface can provide a cold compress effect or cooling effect on skin.

The working principle of the beauty instrument shown in FIG. 27 is the same as that of the previous embodiment.

The beauty instrument of the embodiment shown in FIG. 28 uses the thermoelectric cooling assembly 1 of the above-mentioned third embodiment to cool the light out surface 113 of the beauty instrument. The other structural parts of the beauty instrument are identical or similar to those of the embodiment as shown in FIGS. 16-19. T heat transfer assembly 19 is L-shaped. One end of the heat transfer assembly 19 is installed on the heat sink 16 and is located at the vent of the top of the fan 18. Aluminum Vapor Chambers or Aluminum Heat Pipes 191 are installed on the thermal conductive plate 190 and faces the fan. The heat transfer assembly 10 on the thermal conductive plate 190 is located outside the vent of the fan 18. The heat transfer assembly 19, the fan 18, and the heat sink 16 are all located in the air flow paths in the housing of the beauty instrument, and the respective air flow paths are connected, and are connected by the vents 111 of the housing of the beauty instrument. Cold air is input, takes away heat in the air flow paths in the housing of the beauty instrument, and is then discharged to the outside of the beauty instrument through another vent 111.

The thermoelectric cooler 10 is installed on the platform on one side of the heat conductive plate 190, and the cold side of the thermoelectric cooler 10 is connected to the light out surface 113 of the beauty instrument by the heat transfer component (copper/A Aluminum Heat Pipe/ALVC/heat pipe/VC) 15,15'. The groove 161 (FIG. 22) on the heat sink 16 is used to install one end of the heat conductive plate 190. The air channel between adjacent fins of the heat sink 16 and the air flow path in the fan are in air communication, and are in air communication with reflective cover 21 of the light source assembly 2. The heat transfer member 22 of the reflective cover is located in the vent 182 of the fan 18 or in the air flow path in the beauty instrument for heat dissipation of the reflective cover 21 and the lamp tube 20. In this embodiment, the thermoelectric cooling assembly 1 is used to cool the light out surface 113 and dissipate heat from the light source assembly 2.

The heat transfer assembly 19 of the above embodiments of the present invention uses multiple Aluminum Heat Pipes or Aluminum Vapor Chambers 191 mounted in the thermal conductive plate (such as a copper plate) 190, which can effectively solve the problem of the gravity direction of the instrument.

The technical features of the above embodiments can be combined arbitrarily. In order to make the description simple, all possible combinations of the technical features in the above embodiments are not described. However, as long as there is no contradiction in the combination of these technical features. It is considered to be the range described in this specification.

The above examples only represent several embodiments of the present invention, and the descriptions thereof are specific and detailed, but should not be construed as a limitation on the scope of the invention patent. It should be pointed out that for those of ordinary skill in the art, without departing from the concept of the present invention, several modifications and improvements can also be made, which all belong to the protection scope of the present invention. Therefore, the protection scope of the patent of the present invention should be subject to the appended claims.

What is claimed is:

1. A thermoelectric cooling assembly comprising:

a thermoelectric cooler, comprising semiconductors in the middle and electrically interconnected, a hot side and a cold side at both sides of the semiconductors;

a heat sink; and a heat transfer assembly, comprising:

several aluminum vapor chambers or aluminum heat pipes; wherein each aluminum vapor chamber or aluminum heat pipe is sealed and contains refrigerant inside; micro-grooves are formed on an inner wall of each aluminum vapor chamber or aluminum heat pipe; micropores are formed in materials of each aluminum vapor chamber or aluminum heat pipe; each aluminum vapor chamber or aluminum heat pipe has a single channel therein through a length thereof; and each aluminum vapor chamber or aluminum heat pipe is bent in 2-dimension or 3-dimension; and a thermal conductive plate, forming several grooves therein according to said several aluminum vapor chambers or aluminum heat pipes; wherein each aluminum vapor chamber or aluminum heat pipe is fixed in one groove; walls of the aluminum vapor chamber or aluminum heat pipe and the groove are in contact with each other for heat transfer;

wherein the heat transfer assembly is thermally connected with said heat sink for heat dissipation; and the heat transfer assembly is thermally connected with said hot side or provides said hot side to which the semiconductors are welded.

2. The thermoelectric cooling assembly as claimed in claim 1, the hot side of the thermoelectric cooler is fitted on an outer wall of the thermal conductive plate; or, the heat-conducting plate serves as said hot side to which the semiconductors are welded.

3. The thermoelectric cooling assembly as claimed in claim 1, wherein the heat sink comprises one or more sets of fins, said thermal conductive plate is mounted on and in contact with the fins for contact heat transfer; or the heat sink and the thermal conductive plate are arranged on and in contact with another thermal conductive member for heat transfer therebetween.

4. The thermoelectric cooling assembly as claimed in claim 1, comprising a fan which comprises a casing and rotatable blades in the casing; the casing of the fan comprises a top cover, a bottom cover and a side frame; and the heat transfer assembly is located at a vent of the fan or serves as a part of the casing of the fan.

5. The thermoelectric cooling assembly as claimed in claim 1, comprising a heat transfer component with one end thereof connected to the cold side of the thermoelectric cooler in a rapid heat transfer manner, and the other end in contact with a surface to be cooled; the heat transfer component is a copper tube, a vapor chamber, an aluminum vapor chamber, an aluminum heat pipe, or a heat pipe.

6. A beauty instrument, comprising:

a housing with vents therethrough as an air inlet or air outlet;

a control circuit board in the housing;

a light source assembly in the housing and electrically connected with the control circuit board; and a thermoelectric cooling assembly comprising:

a thermoelectric cooler, comprising semiconductors in the middle and electrically interconnected, a hot side and a cold side at both sides of the semiconductors;

a heat sink;

a first heat transfer component, being a copper tube, a vapor chamber, an aluminum vapor chamber, an aluminum heat pipe, or a heat pipe;

a second heat transfer component, being a copper tube, a vapor chamber, an aluminum vapor chamber, an aluminum heat pipe, or a heat pipe;

a fan; and a heat transfer assembly, comprising a vapor chamber or an aluminum vapor chamber or an aluminum heat pipe;

wherein the heat transfer assembly is thermally connected with said heat sink for heat dissipation, is thermally connected with said hot side or forms said hot side to which the semiconductors are welded, and is located at a vent of the fan or serves as a part of a casing of the fan; a front end of the beauty instrument has a light outlet surface; said cold side of the thermoelectric cooler is connected to and cools the light outlet surface, or said cold side serves as the light outlet surface, thereby, the light outlet surface is able to cool skin on contact;

the second heat transfer component thermally connects between the first heat transfer component and the light outlet surface; the second heat transfer component is annular and fitted to the light outlet surface; the first heat transfer component comprises an annular section in contact with the second heat transfer component, and two ends of the first heat transfer component extending from the annular section closely contact the cold side.

7. The beauty instrument as claimed in claim 6, wherein the light source assembly comprises a lamp tube and a reflective cover, the lamp tube is mounted inside the reflective cover; a space inside the reflective cover is in air communication with the fan for heat dissipation of the light source assembly; a heat transfer member fitted on back of the reflective cover extends to a vent of the fan for heat dissipation, and the heat transfer member comprises thermal conductive fins.

8. The beauty instrument as claimed in claim 6, wherein the beauty instrument is a hair removal device, a photon skin rejuvenation device, an import-export beauty device or a RF beauty device.

9. The beauty instrument as claimed in claim 6, wherein the aluminum vapor chamber or the aluminum heat pipe is sealed, and refrigerant is contained inside; micro-grooves are formed on an inner wall of the aluminum vapor chamber or the aluminum heat pipe; and micropores are formed in materials of the aluminum vapor chamber or the aluminum heat pipe.

10. The beauty instrument as claimed in claim 6, wherein the heat transfer assembly comprises several aluminum vapor chambers or aluminum heat pipes; each aluminum vapor chamber or aluminum heat pipe has a single channel therein through a length thereof; each aluminum vapor chamber or aluminum heat pipe is bent in 2-dimension or 3-dimension; the heat transfer assembly further comprises a thermal conductive plate, said several aluminum vapor chambers or aluminum heat pipes are fixed in the thermal conductive plate.

11. A beauty instrument, comprising:

a housing with vents therethrough as an air inlet or air outlet;

a control circuit board in the housing;

a light source assembly in the housing and electrically connected with the control circuit board; and a thermoelectric cooling assembly comprising:

a thermoelectric cooler, comprising semiconductors in the middle and electrically interconnected, a hot side and a cold side at both sides of the semiconductors;

a heat sink;

a fan; and a heat transfer assembly, comprising:

several aluminum vapor chambers or aluminum heat pipes; wherein each aluminum vapor chamber or aluminum heat pipe has a single channel therein through a length thereof; each aluminum vapor chamber or aluminum heat pipe is bent in 2-dimension or 3-dimension; and a thermal conductive plate, forming several grooves therein according to said several aluminum vapor chambers or aluminum heat pipes; wherein each aluminum vapor chamber or aluminum heat pipe is fixed in one groove; walls of the aluminum vapor chamber or aluminum heat pipe and the groove are in contact with each other for heat transfer;

wherein the heat transfer assembly is thermally connected with said heat sink for heat dissipation, is thermally connected with said hot side or forms said hot side to which the semiconductors are welded, and is located at a vent of the fan or serves as a part of a casing of the fan; a front end of the beauty instrument has a light outlet surface; said cold side of the thermoelectric cooler is connected to and cools the light outlet surface, or said cold side serves as the light outlet surface, thereby, the light outlet surface is able to cool skin on contact.

12. The beauty instrument as claimed in claim 6, wherein the thermoelectric cooler is arranged on the vapor chamber; the hot side of the thermoelectric cooler is in contact with the vapor chamber for rapid heat transfer, or, the hot side and the vapor chamber are thermally connected through a heat transfer component, or, an outer wall of the vapor chamber serves as the hot side of the thermoelectric cooler to which the semiconductors are welded; and the heat sink is arranged on the vapor chamber.

13. The beauty instrument as claimed in claim 6, wherein the fan comprises the casing and rotatable blades in the casing; the casing of the fan comprises a top cover, a bottom cover and a side frame.

14. The beauty instrument as claimed in claim 13, wherein the heat transfer assembly comprises the vapor chamber which is located at the vent of the fan or serves as a part of the casing of the fan.

15. The beauty instrument as claimed in claim 14, wherein the vapor chamber serves as the side frame, and an inner wall of vapor chamber is provided with fins thereon.

16. The beauty instrument as claimed in claim 14, wherein the vapor chamber serves as the top or bottom cover of the fan, which covers a top opening or a bottom opening of the casing.

17. The beauty instrument as claimed in claim 14, wherein the heat sink is set on the vapor chamber.

18. The beauty instrument as claimed in claim 14, wherein the vapor chamber is an annular flat plate with a central through hole as a vent of the fan, and the heat sink covers the central through hole.

19. The beauty instrument as claimed in claim 14, wherein the vapor chamber is an annular flat plate with a central through hole as a vent of the fan, the heat sink is arranged along an annular edge of the central through hole.

* * * * *